United States Patent
Akallal et al.

(10) Patent No.: US 11,737,742 B2
(45) Date of Patent: *Aug. 29, 2023

(54) DEVICES, APPARATUS AND METHODS FOR PATIENT-SPECIFIC MIS PROCEDURES

(71) Applicant: SpineCraft, LLC, Westmont, IL (US)

(72) Inventors: Mohammed Akallal, Naperville, IL (US); Wagdy W. Asaad, Burr Ridge, IL (US)

(73) Assignee: Spine Craft, LLC, Westmont, IL (US)

( * ) Notice: Subject to any disclaimer, the term of this patent is extended or adjusted under 35 U.S.C. 154(b) by 372 days.

This patent is subject to a terminal disclaimer.

(21) Appl. No.: 17/190,633

(22) Filed: Mar. 3, 2021

(65) Prior Publication Data
US 2022/0249083 A1    Aug. 11, 2022

Related U.S. Application Data

(63) Continuation-in-part of application No. 17/169,435, filed on Feb. 6, 2021, now Pat. No. 11,534,183.

(51) Int. Cl.
*A61B 17/02* (2006.01)
*A61B 34/20* (2016.01)

(52) U.S. Cl.
CPC ........ *A61B 17/0218* (2013.01); *A61B 17/025* (2013.01); *A61B 17/0206* (2013.01); *A61B 34/20* (2016.02); *A61B 2017/0256* (2013.01)

(58) Field of Classification Search
CPC ................................................. A61B 17/0218
See application file for complete search history.

(56) References Cited

U.S. PATENT DOCUMENTS

| 8,100,951 | B2 | 1/2012 | Justis et al. |
| D705,929 | S | 5/2014 | Frey |
| 8,864,769 | B2 | 10/2014 | Stone et al. |
| D745,671 | S | 12/2015 | Frey et al. |
| 9,642,633 | B2 | 5/2017 | Frey et al. |
| 9,987,024 | B2 | 6/2018 | Frey et al. |

(Continued)

FOREIGN PATENT DOCUMENTS

| EP | 2502582 | 11/2016 |
| EP | 2749235 | 8/2017 |
| KR | 101974287 | 4/2019 |

OTHER PUBLICATIONS

English translation of KR101974287.

*Primary Examiner* — Christian A Sevilla
(74) *Attorney, Agent, or Firm* — Law Office of Alan W. Cannon

(57) ABSTRACT

Devices, apparatus and methods for patient-specific MIS procedures. A patient-specific, MIS navigation guide device may include a main body having a proximal surface and a distal surface, wherein the distal surface is configured to face target tissue upon placement of said MIS navigation guide device. Anchors extend distally of the distal surface, and distal ends of the anchors lie on a three dimensional surface that matches contours of the target tissue in locations where the anchors are designed to contact. A position indicator on the device is interpretable by a surgeon to know when the anchors have not yet been contacted to the target tissue in a predetermined orientation and to know when the anchors have been contacted to the target tissue in the predetermined orientation.

20 Claims, 14 Drawing Sheets

(56) References Cited

U.S. PATENT DOCUMENTS

| | | |
|---|---|---|
| 10,524,831 B2 | 1/2020 | Mather et al. |
| 10,806,470 B2 | 10/2020 | Lipari et al. |
| 2006/0142656 A1* | 6/2006 | Malackowski ........ A61B 90/39 |
| | | 600/424 |
| 2007/0066887 A1* | 3/2007 | Mire ...................... A61B 90/39 |
| | | 600/424 |
| 2007/0198022 A1* | 8/2007 | Lang .................. A61B 17/1666 |
| | | 606/88 |
| 2009/0157083 A1* | 6/2009 | Park .................. A61B 17/1725 |
| | | 606/88 |
| 2013/0145812 A1 | 6/2013 | Kawaguchi |
| 2013/0338673 A1* | 12/2013 | Keppler ............. A61B 17/1778 |
| | | 606/86 R |
| 2014/0180295 A1* | 6/2014 | Buza ...................... A61B 17/15 |
| | | 29/592 |
| 2014/0358152 A1 | 12/2014 | Condino et al. |
| 2016/0199198 A1 | 7/2016 | Dietz et al. |
| 2016/0270816 A1 | 9/2016 | Mather et al. |
| 2017/0135706 A1 | 5/2017 | Frey et al. |
| 2017/0311961 A1 | 11/2017 | Lipari et al. |
| 2018/0116727 A1 | 5/2018 | Caldwell et al. |
| 2018/0271602 A1 | 9/2018 | Frey et al. |

* cited by examiner

DEVICES, APPARATUS AND METHODS FOR PATIENT-SPECIFIC MIS PROCEDURES

CROSS-REFERENCE

This application is a continuation-in-part application of Ser. No. 17/169,435, filed Feb. 6, 2021, which is incorporated herein, in its entirety, by reference thereto, and to which application we claim priority under 35 USC § 120.

FIELD OF THE INVENTION

The present invention relates to the field of orthopedic surgery, in particular to devices and methods for patient-specific 3D surgical planning. More particularly devices and methods of minimally-invasive surgery are provided.

BACKGROUND OF THE INVENTION

The use of various 3D visualization technologies have been used to provide 3D mapping data that can be used via computer-aided design (CAD) and/or finite element modeling (FEM) to produce patient-specific models of select portions of a patient's anatomy and to design implants and/or procedures that take into account the specific characteristics of the patient's anatomy having been measured and mapped. As anatomy can vary from patient to patient, these techniques are very useful in accounting for unique and varying anatomical features that may be encountered in a particular patient.

For example, the implantation of pedicle screws in vertebral bodies is a common practice for treatment of various spine pathologies. The implantation can be performed by using anatomical landmarks as references for placement and delivery angulation of the screws to be implanted. However due to variations in anatomy among patients, as well as other factors, including human error, this approach runs considerable risks in the possibility of breaching the pedicle, with a potential to cause neurological injuries. Although visualization of the procedure using fluoroscopy can be performed during the implantation to reduce these risks, the risks are still considerable.

Other visualization techniques that have been used include image guided techniques requiring cameras and infra-red sensors, specialized instrumentation with directional sensors embedded into the device, etc. These increase the costs of the procedures as well as the time required to complete the procedures.

The use of magnetic resonance imaging (MRI) data or computed tomography (CT) data for conversion into a data set readable by computer-aided design (CAD) program and/or finite element modeling (FEM) program, has been used to create a custom implant based on the dynamic nature of the anatomical structures the custom implant is designed to associate with. While these techniques have been used for surgery planning, the resulting plans and techniques used are typically open procedures that are at least as invasive as the plans and techniques used for implantation of standardized implants.

There is a continuing need to provide patient-specific surgical planning and patient-specific devices that are less invasive than those currently known and used, to reduce costs and reduce patient recovery time, pain experienced, etc.

There is a continuing need to provide patient-specific surgical planning and patient-specific devices that are less invasive and reduce the time needed to perform a surgical procedure.

SUMMARY OF THE INVENTION

In one aspect of the present invention, a patient-specific, MIS navigation guide device is provided that includes: a main body having a proximal surface and a distal surface, wherein the distal surface is configured to face target tissue upon placement of the MIS navigation guide device; anchors extending distally of said distal surface, wherein distal ends of the anchors lie on a three dimensional surface that matches contours of the target tissue in locations where the anchors are designed to contact; and a position indicator on the device; wherein the position indicator is interpretable by a surgeon to know when the anchors have not yet been contacted to the target tissue in a predetermined orientation and to know when the anchors have been contacted to the target tissue in the predetermined orientation.

In at least one embodiment, the device includes a retractor mount configured to dock a retractor over the proximal surface of the device.

In at least one embodiment, the guide device is configured to guide the performance of a surgical operational step on the target tissue along an optimal, predefined pathway.

In at least one embodiment, the position indicator includes at least two position indicators with one of the position indicators being located on an opposite side of the main body, relative to a location of another of the at least two position indicators In at least one embodiment, the device includes: a first pair of generally opposing jaw surfaces formed on a first portion of the main body; and a second pair of generally opposing jaw surfaces formed on a second portion of the main body, wherein the second portion is on an opposite side of the main body to a side of the main body on which the first portion is located.

In at least one embodiment, the first pair of generally opposing jaw surfaces are configured to contact a specific spinous process of a specific vertebra of a specific patient and the second pair of generally opposing jaw surfaces are configured to contact a specific transverse process of the specific vertebra of the specific patient.

In at least one embodiment, the specific vertebra is the S1 vertebra.

In at least one embodiment, the first pair of generally opposing jaw surfaces are configured to contact a specific process of a specific vertebra of a specific patient and the second pair of generally opposing jaw surfaces are configured to contact another specific process of the specific vertebra in the cervical spine of the specific patient.

In at least one embodiment, the first pair of generally opposing jaw surfaces are configured to contact a specific process of a specific vertebra in the thoracolumbar spine of a specific patient and the second pair of generally opposing jaw surfaces are configured to contact another specific process of the specific vertebra in the thoracolumbar spine of the specific patient.

In at least one embodiment, the guide device further comprises a bore through the main body located to match a point of entry of a screw to be implanted in the target tissue; and a trajectory guide aligned with the bore and configured to guide a drill along an optimal axis of implantation of the screw in the target tissue.

In at least one embodiment, the device is configured to contact the target tissue on at least six predefined locations ($M_1$, $M_2$, $M_3$, $M_4$, $M_5$, $M_6$) conforming to the following conditions: at least three of the at least six predefined locations are located on one side of the device, relative to the bore through the main body; at least three others of the at least six predefined locations are located on an opposite side of the device, relative to the bore; the sides are defined relative to a line that passes through the bore and is aligned with the sagittal plane of the patient, when the device is mounted as desired relative to the target tissue; and for locations $M_i$ and $M_j$ both located on the same one of the sides, $\cos \theta_{ij} \leq \frac{1}{4}$, where $i \neq j$ and $i,j=1, 2 \ldots 6$; $\theta_{ij}$ is the angle formed by any two normal vectors to the surface of the device of respectively at locations $M_i$ and $M_j$; for each $M_i$ on the one side and for each $M_j$ on the opposite side, with $\vec{k}$ defined as a normal vector to a surface of contact on the target tissue at the point $M_i$ where the device contacts the target tissue, and $\vec{i}$, $\vec{j}$ are two normal vectors to the vector $\vec{k}$ with $\|\vec{i}\|=\|\vec{j}\|=\|\vec{k}\|=1$ (with 1 unit=1 mm); wherein T is a transformation defined by a matrix M, where M represents any combination of translations or rotations, and S is the surface of contact of the device along which it contacts the target tissues of the patient matching anatomy; $M_i'=T(M_i)$; where ($x_i$, $y_i$, $z_i$) are the coordinates of $M_i'$ in the axis system $\vec{i}$, $\vec{j}$, $\vec{k}$, if $-3<x_i<3$, $-3<y_i<3$ and $-3<z_i<3$; and if $M_i' \in S$; then $M_j' \notin S$; and $M_j'=T(M_j)$ ($x_j$, $y_j$, $z_j$) are the coordinates of $M_j'$ in the axis system $\vec{i}$, $\vec{j}$, $\vec{k}$ if $-3<x_j<3$, $-3<y_j<3$ and $-3<z_j<3$; and if $M_j' \in S$; then $M_i' \notin S$.

In at least one embodiment, the guide is provided in combination with a tubular MIS retractor, wherein the guide device is configured to be delivered through the tubular MIS retractor to the target tissue by an MIS surgical procedure.

In at least one embodiment, the tubular MIS apparatus comprises a slot that extends lengthwise and is configured to allow a tool to slide therein.

In at least one embodiment, the MIS navigation guide device is provided in in combination with an MIS delivery tool, wherein the delivery tool is configured to releasably attach to the guide device and is articulatable to rotate an orientation of the guide device.

In at least one embodiment, the device and tool are provided in combination with a tubular MIS retractor, wherein the tool is configured to deliver the guide device through the tubular MIS retractor to the target tissue during an MIS surgical procedure.

In at least one embodiment, the tubular MIS retractor includes a slot that extends lengthwise and is configured to allow the tool to slide therein.

In at least one embodiment, the navigation guide device includes a retractor mount configured to dock the retractor over the proximal surface of the device.

In at least one embodiment, the retractor mount comprises arcuate slots on locations opposite the operational guide and configured to receive distal end portions of the retractor.

In at least one embodiment, the device, tool and retractor are configured for use in MIS percutaneous spine surgeries.

In at least one embodiment, the anchors upon contacting the target tissue create a space between the distal surface of the main body and the contours of the target tissue.

In at least one embodiment, different ones of the anchors are oriented at different angles relative to one another to enhance slippage prevention of the device relative to the target tissues upon contact of the anchors thereto.

In at least one embodiment, the anchors conform to the contours of the target tissue to securely dock the device to the target tissue and the anchors have sharp or pointed ends to further enhance securement.

In at least one embodiment, the three-dimensional surface and configuration of the guide are defined using data derived from anatomical data obtained from computed tomography images of the specific patient.

In another aspect of the present invention, an MIS navigation apparatus includes: a patient-specific, MIS navigation guide device having: a main body having a proximal surface and a distal surface, wherein the distal surface is configured to face target tissue upon placement of the MIS navigation guide device; anchors extending distally of the distal surface, wherein distal end of the anchors lie on a three dimensional surface that matches contours of the target tissue in locations where the anchors are designed to contact; and a retractor mount; and a tubular MIS retractor comprising; an elongate tubular body dimensioned for MIS surgical procedures; wherein the guide device is configured to be delivered through the tubular MIS retractor to the target tissue during an MIS surgical procedure; and wherein the tubular retractor is configured to be withdrawn slightly to allow delivery of the device out of a distal end of the retractor; and wherein the retractor mount is configured to receive a distal end portion of the retractor to dock the retractor to the device.

In at least one embodiment, the target tissue is of a specific vertebra of a specific patient.

In at least one embodiment, the specific vertebra is the S1 vertebra.

In at least one embodiment, the specific vertebra is a specific vertebra in the cervical spine of the specific patient.

In at least one embodiment, the specific vertebra is a specific vertebra in the thoracolumbar spine of the specific patient.

In at least one embodiment, the tubular MIS apparatus includes a slot that extends lengthwise and is configured to allow a tool to slide therein.

In another aspect of the present invention, an MIS navigation apparatus includes: a patient-specific, MIS navigation guide device having: a main body having a proximal surface and a distal surface, wherein the distal surface is configured to face target tissue upon placement of the MIS navigation guide device; and anchors extending distally of the distal surface, wherein the distal ends of the anchors lie on a three dimensional surface that matches contours of the target tissue in locations where the anchors are designed to contact; and an MIS delivery tool configured to releasably attach to the guide device, the tool being articulatable to rotate an orientation of the guide device; wherein the tool is configured to deliver the guide device through the tubular MIS retractor in a first orientation and to rotate the guide device, once distal of the MIS retractor to a second orientation to match contours of the target tissue.

In at least one embodiment, the target tissue is of a specific vertebra of a specific patient.

In at least one embodiment, the specific vertebra is the S1 vertebra.

In at least one embodiment, the specific vertebra is a specific vertebra in the cervical spine of the specific patient.

In at least one embodiment, the specific vertebra is a specific vertebra in the thoracolumbar spine of the specific patient.

In at least one embodiment, the device further includes: an operational guide configured to guide the performance of a surgical operational step on the target tissue along an optimal pathway predefined by the operational guide relative to the main body; and a position indicator on the device; wherein the position indicator is interpretable by a surgeon to know when the anchors have not yet been contacted to the target tissue in a predetermined orientation and to know when the anchors have been contacted to the target tissue in the predetermined orientation.

In another aspect of the present invention, a minimally-invasive surgical procedure includes: inserting an MIS retractor through an incision and into a pathway formed in a patient over target tissue until a distal end of the retractor contacts or approximates the target tissue; delivering an MIS, patient-specific device through the retractor using a tool releasably attached to the device; partially withdrawing the MIS retractor to define a space between the distal end of the retractor and the target tissue sufficient to deliver the device into; rotating the device when distal of the distal end of the retractor and contacting the device to the target tissue, wherein the target tissue is of a specific vertebra of a specific patient; docking the retractor into a mating feature of the device; and performing at least one operational step on the specific vertebra through the retractor, guided by the MIS, patient-specific device.

In at least one embodiment, the specific vertebra is the S1 vertebra.

In at least one embodiment, the specific vertebra is a specific vertebra in the cervical spine of the specific patient.

In at least one embodiment, the specific vertebra is a specific vertebra in the thoracolumbar spine of the specific patient.

In at least one embodiment, the procedure further includes; again partially withdrawing the MIS retractor to define a space between the distal end of the retractor and the target tissue; and withdrawing the device through the retractor and out of the patient.

In at least one embodiment, the procedure further includes performing one or more further operational steps on the target tissue through the retractor.

In at least one aspect of the present invention, surgical guides are provided that can be used in minimally invasive surgeries, which is advantageous as surgical guides that existing prior to the present invention cannot be used in minimally invasive surgeries as they cannot be deployed as an integral unit through an MIS retractor.

At least one aspect of the present invention allows accurate screw placement in the S1 Vertebra with minimum use of fluoroscopy and reduced exposure to radiation for patients and surgeons. A customized guide can be provided for each screw that is placed.

At least one aspect of the present invention allows accurate pedicle screw placement in the cervical spine with minimum use of fluoroscopy and reduced exposure to radiation for patients and surgeons. A customized guide can be provided for each pedicle screw that is placed.

At least one aspect of the present invention allows accurate pedicle screw placement in the thoracolumbar spine with minimum use of fluoroscopy and reduced exposure to radiation for patients and surgeons. A customized guide can be provided for each pedicle screw that is placed.

These and other advantages and features of the invention will become apparent to those persons skilled in the art upon reading the details of the devices, apparatus and methods as more fully described below.

BRIEF DESCRIPTION OF THE DRAWINGS

In the course of the detailed description to follow, reference will be made to the attached drawings. These drawings show different aspects of the present invention and, where appropriate, reference numerals illustrating like structures, components, materials and/or elements in different figures are labeled similarly. It is understood that various combinations of the structures, components, materials and/or elements, other than those specifically shown, are contemplated and are within the scope of the present invention.

DETAILED DESCRIPTION OF THE INVENTION

Figure 1:
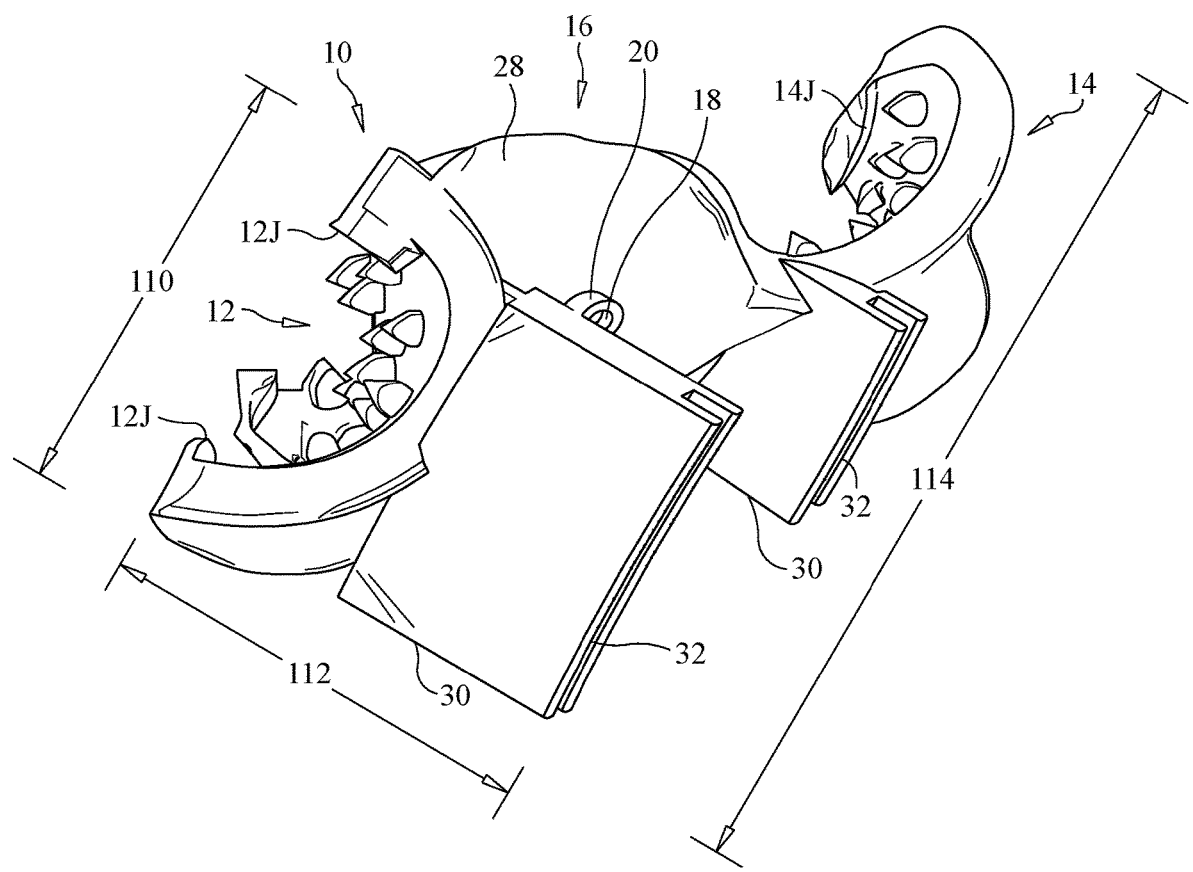
FIG. 1 is a perspective illustration of a navigational guide device according to an embodiment of the present invention.

Before the present devices, apparatus and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "an anchor" includes a plurality of such anchors and reference to "the position indicator" includes reference to one or more position indicators and equivalents thereof known to those skilled in the art, and so forth.

The publications discussed herein are provided solely for their disclosure prior to the filing date of the present application. The dates of publication provided may be different from the actual publication dates which may need to be independently confirmed.

Definitions

An "MIS navigation guide", as used herein, refers to a device that is sized and configured to be inserted through a minimally-invasive retractor, tube, cannula or other tool used for delivery of a device to a surgical target using a minimally invasive (MIS) procedure. Although designed particularly for use in MIS procedures, an MIS navigation guide can also be used in an open surgical procedure or other surgical procedure than an MIS procedure.

As shown and described in detail herein, the present disclosure relates to novel and inventive apparatus, systems and methods for patient-specific 3D surgical planning, including, but not limited to planning, making and using customized, patient-matched apparatus for use in a diverse number of surgical procedures, specifically for minimally-invasive procedures, but which could be used for open procedures and other types of procedures as well. The planning and manufacturing of apparatus are tied to the specific anatomy of a particular patient, and data used in the planning and manufacturing may be derived from capturing CT data, MRI data, or any other medical imaging device that can be used to record three dimensional data characterizing the patient anatomy. This data can then be used to design apparatus that conforms to the morphology of an anatomical surface that the apparatus is to be contacted to, thereby form a customized fit. According to various embodiments described herein, the patient-matched apparatus may further comprise desired axes and/or insertional trajectories. Other features of the disclosure will become apparent after a review of the following disclosures and varying embodiments of the present invention.

FIG. 1 is a perspective illustration of a navigational guide device 10 according to an embodiment of the present invention. The guide 10 of FIG. 1 is a patient-specific 3D surgical planning navigational guide that is designed specifically to fit anatomical contours of a specific vertebra of a specific patient, and which can be used in minimally invasive spinal surgery. In the embodiment shown, the guide 10 is designed for a specific L3 vertebra, but this embodiment can be specifically designed according to principles described herein for any specific vertebra of a specific patient in the cervical or thoracolumbar spine. Of course guide 10 could also be used in open spinal surgery or other types of endoscopic spinal surgery. Also, although the present disclosure is directed mainly toward minimally-invasive spinal surgery, the present invention may alternatively be used for patient-specific 3D surgical planning and MIS surgical procedures on anatomy other than the spine.

Thus the present invention discloses guides that are patient-specific MIS (minimally-invasive surgery) navigational guides, to be used as disposable templates, which are individually designed to match the bone anatomy obtained from computed tomography images or other 3-dimensional data measuring the bone anatomy of a particular patient. Surgical procedures can be pre-operatively planned by computer-aided technologies, and the resulting patient-specific guides will then allow the surgeon to accurately replicate the planned operations. The three-dimensional data may be captured from a MRI or CT scan or from radiographic images of the patient's corresponding boney anatomy (or alternatively from other data sources). The data, once captured, may be converted using known software tools to a computer aided design (CAD) program, where the data set is representative of the patient's anatomy and may be used to provide additional data points for forming the contours, sizes, shapes and orientations of one or more apparatus to be used in the surgical procedure.

The device 10 of FIG. 1 can be used to assist a surgeon during a percutaneous pedicle screw insertion in a minimally invasive surgery procedure, so that the pedicle screw can be inserted along a pre-planned optimum axis thereof. Surgeons pre-operatively indicate an optimal screw trajectory along which the optimum axis is defined and then the patient-specific guide can be designed to mechanically constrain a drill, and consequently the pedicle screw, to follow that trajectory.

The device 10 can be integrally manufactured as a single piece and is configured and dimensioned to be delivered percutaneously through a retractor to a target site using a minimally invasive procedure. Once the device 10 has been delivered to the target site, the retractor can be slightly withdrawn, but not out of the body, to that the retractor can be mounted or docked in arcuate slots 32 of retractor mounts 30 that extend proximally from the proximal surface 28 of the main body of device 10. In the embodiment of FIG. 1, retractor mounts 30 extend proximally from the surface 28 at the locations of the wings 12 and 14.

Figure 2:
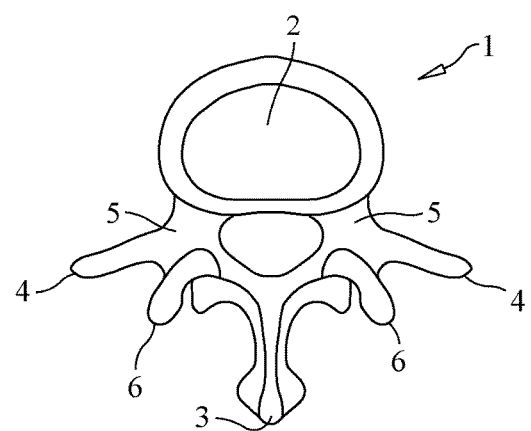
FIG. 2. shows a plan view of a human vertebra.

FIG. 2 shows a plan view of a human vertebra 1. Shown are the vertebral body 2 and various other feature and articulations that can be used for 3D design of a guide configured to be placed into apposition with such features which act as landmarks to ensure proper placement and orientation of the guide 10. Features that the guide may be specifically designed to be placed in apposition with include, but are not limited to the transverse process 4, lamina 5 and/or articular process 6 (such as superior articular process) and/or spinous process 3.

Referring again to FIG. 1, device 10 is an integral guide that is configured to be inserted through a retractor (e.g., slotted, tubular guide) to be placed in apposition with a vertebra during an MIS procedure. Because the device 10 does not need to be disassembled or otherwise delivered in parts and then assembled/reassembled at the surgical site, this greatly simplifies the procedure and also reduces the time needed to carry out the procedure. In the embodiment of FIG. 1, device 10 includes a first wing portion 12, a second wing portion 14, and an intermediate portion 16 between the first and second wing portions 12, 14.

The anchors 22 extend from the lower surfaces 24 of the portions 12, 14 and 16 and are contoured to dock in apposition to anatomical features on a specific vertebra 1 of a specific patient, such that the device can be docked in only one specific orientation that accurately aligns it to establish a trajectory guide along an optimum axis for implanting a pedicle screw along an optimum trajectory into the vertebra. Multiple anchors 22 extend from the lower surfaces. Typically at least fifteen anchors 22 are provided but the number of anchors may range from about 10 to 60, typically 15 to 50. In one specific example, the total number of anchors 22 was 45. By using at least 15 anchors 22, this allows at least three anchors to be positioned around each of the position indicators 26 and at least three anchors 22 to be docked on each of the transverse process and the articular process or spinous process.

The contours and configuration of the device 10 can be obtained at least in part by use of data generated from scanning the specific patient's anatomy (e.g., one or more specific vertebrae) by CT scan, MRI scan or other 3D visualization technology, and converting the data to 3D data characterizing at least the contours of anatomical features of interest. The 3D data can be used to determine an optical axis, defined in three dimensions relative to the specific vertebra, along which a pedicle screw is to be driven in to the specific vertebra, at a specific location which can also be determined from the 3D data. The three-dimensional contours of the specific anatomy of interest can also be defined by the 3D data and used to construct the contours of the wings 12, 14 and intermediate portion 16 on the sides thereof that are to be placed in apposition to the specific features of interest of the anatomy. The placement and angulation of a bore 18 and optimal axis guide 20 are also established in the device 10 relative to the apposition surfaces of the portions 12, 14 and 16, through the use of the 3D data. From this, device 10 can be modeled and constructed by additive manufacturing techniques, such as 3D printing, rapid prototyping, stereolithography, selective laser sintering, selective heat sintering, fused deposition modeling, direct metal laser sintering, powder bed printing, digital light processing, selective laser melting, inkjet photo resin, or electron beam melting.

In the embodiment of FIG. 1, wing portion 12 is configured to follow the contours of the transverse process 4, intermediate portion 16 is configured to follow the contours of lamina 5 and wing portion 14 is configured to follow the contours of the articular process 6. Of course, this is only one specific embodiment of the present invention and guides 10 can be configured to be placed in apposition to other specific anatomical features to ensure only one correct placement and orientation of the guide during a procedure. This can be accomplished by aligning the contact points of the guide 10 along a contour surface that matches the contours of the anatomy to which the guide 10 is to be contacted. Such anatomical features may be other features of a vertebra, or a guide may be configured to be placed in apposition to some other anatomical feature other than a vertebra, typically, another bony structure, although not necessarily limited to this.

Figure 3:
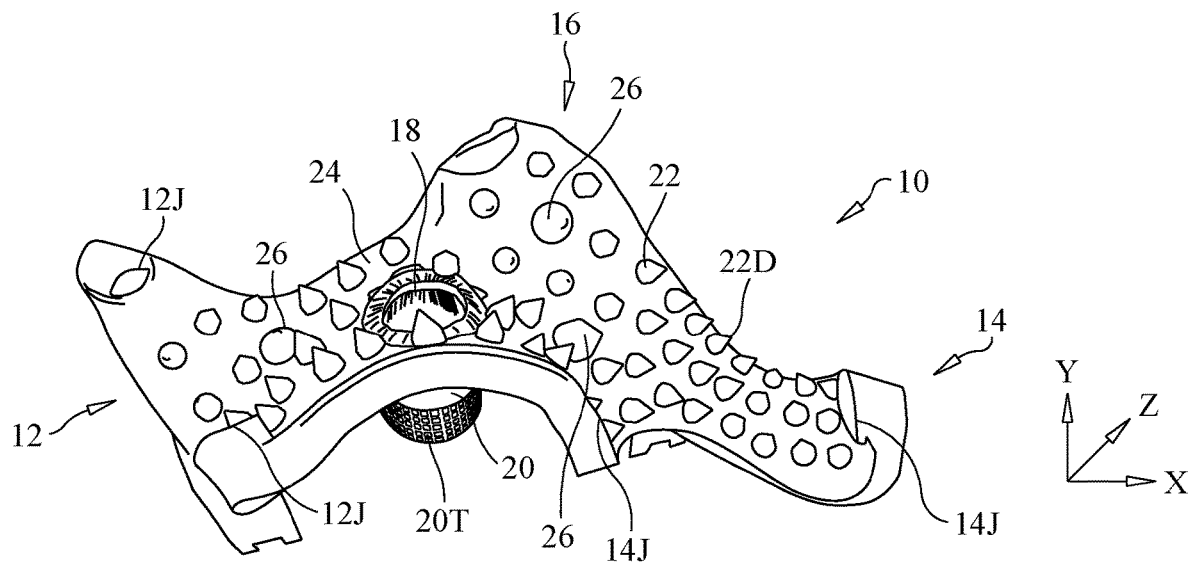
FIG. 3 shows the distal surface of the guide device of FIG. 1.

FIG. 3 shows the underside (distal surface) of guide device 10 which shows the contoured surfaces of portions 12, 14 and 16 that are configured to be placed to conform in apposition to specific anatomic features of a specific patient. Anchors 22 extend from the apposition surfaces 24 and are configured to contact target tissues of the anatomy and prevent the device 10 from sliding relative to the anatomy to which it is contacted, once the device has been properly oriented. The anchors 22 may be spikes, screws, nails or other features that extend from the surface 24 and end with a point or other non-slip configuration 22D. The free (pointed) ends 22D of the anchors extend from the contoured surfaces 24 by distances that maintain the matching contour to the anatomical surface that they are to contact. Thus, for example, if a 3D topological map of the points 22D of anchors 22 is plotted, the topological map conforms to the contours of the anatomical features that the points 22D are to be placed in contact with. The undersurface 24 from which the anchors 22 extend may also be contoured (but not necessarily) to match the contours of the anatomical features that the device 10 is to be placed into contact with via anchors 22.

A number of position indicators 26 are provided in device 10 that are used to indicate when the device 10 has been properly docked against the specific patient's anatomy in the correct position and orientation. In the embodiment of FIGS. 1 and 3, three position indicators 26 are provided as sliding indicators. Although more or fewer than three position indicators 26 may be used, and position indicators other than sliding position indicators may be used (e.g., indicators with switches that activate upon contact with the target to turn on a light or other visible or audible indication, or other mechanical indicator) it is preferred to use at least three sliding position indicators. It is further preferred to provide at least one position indicator 26 closer to one end (along the longest or length dimension) of the device than bore 18 and at least one at least one position indicator 26 closer to the opposite end (along the longest or length dimension) of the device than bore 18. The sliding position indicators 26 are similar to the anchors 22 in that they extend from the surface 24. Sliding indicators may be formed with pointed ends, but need not be. The sliding indicators 26 may have the same diameter as the diameter of the anchors 22, or may be smaller, or larger, such as the ones shown in FIG. 3. An important distinction relative to the anchors 22, is that the sliding indicators 26 are slidable relative to the main body of the device 10 and thus slidable relative to the surface 24, such that the distance of the free end of a sliding indicator 26 from the surface 24, is variable. The sliding indicators 26 are originally configured in the device 10 so that they extend further from the surface than the anchors 22, thus ensuring that they extend beyond the topological surface that conforms to the topology of the anatomical features to which the device is to be placed into apposition. FIG. 3 illustrates the sliding indicators 26 extending further out of the surface 24 than the surrounding anchors 22. When the device 10 is installed on the anatomy that it is designed to fit over, the free ends of the sliding indicators 26 contact the anatomical structures (e.g., bone surface) first. As the device is pushed further against the anatomy, the sliding indicators slide further into the device 10 until they conform with the ends 22D so that they match the contour of the anatomical feature that they are contacting. Once the ends 22D contact the anatomy and cannot be pushed any further into the bone, the sliding indicators 26 also cannot be slid any further relative to the body of the device 10.

Device 10 may also include jaws that oppose one another and have faces that face towards one another and are configured to contact the anatomy in opposition to one another to grossly position the anatomy that they contact to prevent sliding of the device 10 relative to the anatomy. FIG. 3 shows jaws 12J in opposition to one another, configured to contact surfaces of the transverse process to prevent sliding of the wing 12 in directions along which the jaws 12J oppose one another. Likewise, jaws 14J are configured to apply opposing contact to the articular process to prevent sliding along directions in which the jaws 14J oppose one another. Optimal axis guide 20 is an integral part of the device that extends and defines bore 18 along an optimal trajectory for drilling to provide an optimum pathway to implant a pedicle screw.

Figure 4:
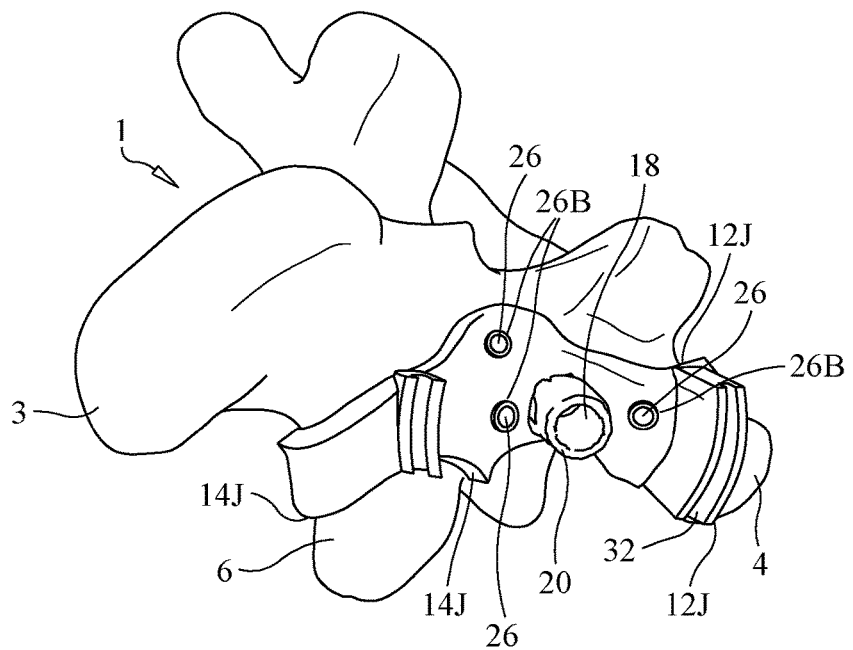
FIG. 4 shows a guide device having been properly docked in apposition against a vertebra of a patient, according to an embodiment of the present invention.

FIG. 4 illustrates device 10 having been properly docked in apposition against a vertebra 1 of a patient. More specifically, jaws 14 contact against the articular process in opposite directions and prevent the device 10/wing 14 from sliding across the articular process 6 (in left-right directions shown in FIG. 4). Jaws 12J contact against the transverse process 4 and prevent the device 10/wing 12 from sliding across the transverse process 4 (in up-down directions shown in FIG. 4). The jaws 12J, 14J also help to orient the device 10 in the correct two-dimensional position relative to the patient's bones, i.e., a correct placement in the X-Y plane illustrated by the plane of the paper that FIG. 4 is shown in. For correct three-dimensional placement and docking, the device 10 is pressed against the target surface forcing the anchors 22 into contact with the target contours. This also drives the position indicators 26 into conformity with the conforming surfaces defined by the ends of the anchors 22 and indicators 26 as they contact the target surface. Once completely docked, the proximal ends 26P of the indicators 26 show visibly as they fill the indicator bores 26B as shown in FIG. 4. The proximal ends 26P may optionally be colored with a color that sharply contrasts with the color of the device 10/indicator bore 26B ring, so that they can be easily seen. Proximal ends 26P are not visible until the device 10 has been properly contacted and oriented to the target contact surface in a three-dimensional relationship. Once properly placed (properly docked), the optimal axis guide 20 has a longitudinal axis passing through bore 18 that defines the optimal trajectory along which to drill the bone to provide the optimum delivery pathway for installation of a pedicle screw.

Figure 5:
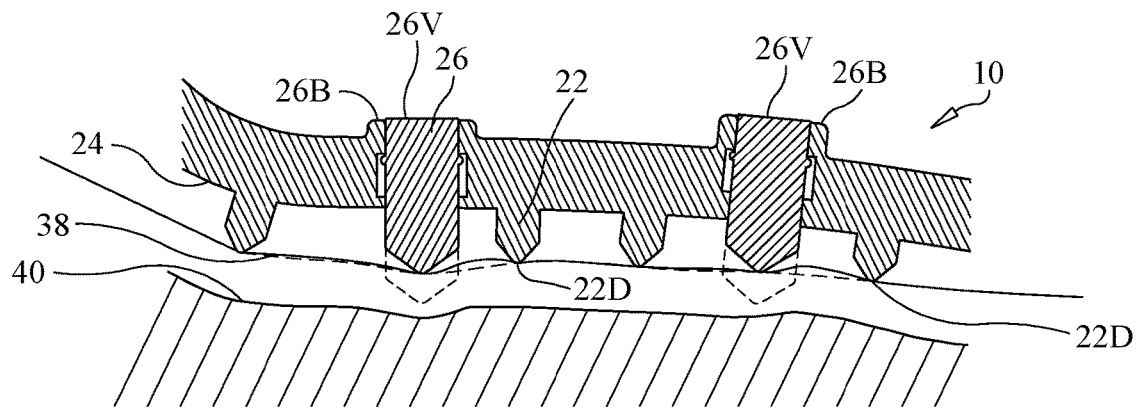
FIG. 5 is a partial sectional illustration demonstrating that the ends of the anchors of a device can be joined to form (or lie in) a topographical surface that conforms to the contours of the target tissue that the device is designed to be contacted/docked to, according to an embodiment of the present invention.
Figure 6:
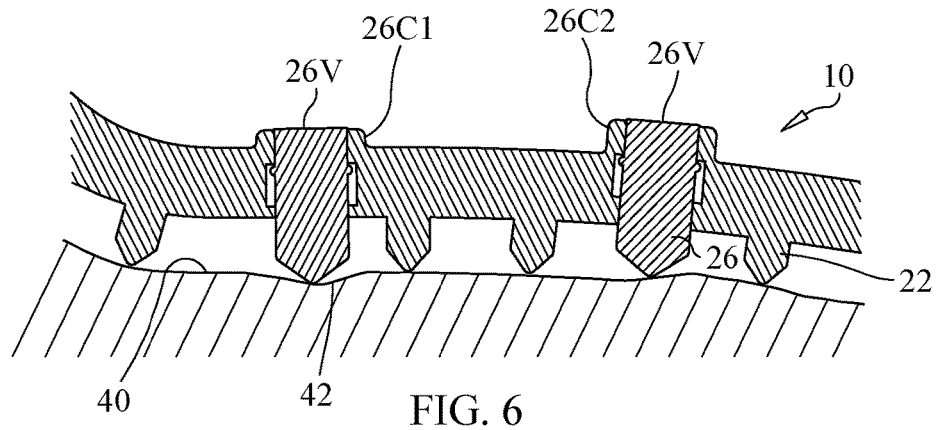
FIG. 6 illustrates the matching conformation of the ends of the anchors and sliding indicators of a device in contact with the contours of the target tissue, according to an embodiment of the present invention.

FIG. 5 is a partial sectional illustration demonstrating that the ends 22D of the anchors are can be joined to form a topographical surface 38 that conforms to the contours 40 of the target tissue that the device is designed to be contacted/docked to. The distal ends of the sliding indicators 26 are initially positioned to extend beyond the matching contour defined by the anchors 22 and this is illustrated by the phantom portions of the indicators 26 in FIG. 5. Upon pressing the device 10 against the target tissues, this causes the sliding indicators 26 to be slid proximally relative to the surface 24 of the device until the distal ends of the indicators 26 come into alignment with the surface 38, as shown in solid lines in FIG. 5. This at the same time causes the visual indicators/proximal ends 26V to become visible as they fill the proximal ends of the bores 26B, thereby indicating that the device 10 has been properly docked with the target tissue. FIG. 6 illustrates the matching conformation of the ends of the anchors 22 and sliding indicators 26 in contact with the contours 40 of the target tissues. Although FIGS. 5-6 show the matching conformation in only one cross-sectional plane, it is noted that this matching conformation occurs in all cross-sectional planes, as the surface of the target tissue is confirmed to by the device 10 in three dimensions: width, length and depth. Because of the unique surface topography of a specific patient, the conforming topography formed by the ends of the anchors 22 and indicators 26 as in FIG. 6 ensures that there can be only a single correct placement of the device 10 in contact with the target tissue. Rotation or translational displacement of the device from the correct orientation against the target tissue would cause one or more of the anchors 22 and/or position indicators 26 to no longer contact the target tissue. The gross positioning of the device 10 by the jaw features 12J, 14J aligns the device correctly relative to length and width directions and pressing the device 10 against the target tissues until position indicators 26 indicate that all anchors 22 and indicators 26 have contacted the target tissues correctly place the device with regard to depth. FIG. 3 illustrates the lack of symmetry about the X, Y and Z axes of the surface 24 as well as the surface that the ends 22D that anchors 22 lie on. This unique surface topography ensures that the device 10 can be properly docked against the target tissues in only one planned orientation.

Small surface irregularities that are difficult to reproduce in the contouring of the device surface 24 can be compensated for by altering the height of the collar that defines the bore 26B that receives indicator proximal end 26V. For example, a revision or a fusion mass or other change to the bone structure may result in a recessed or raised portion of a surface of the target bone that is difficult to position the guide 10 to. In such instances, the majority of the guide 10 can be constructed to conform as in all normal cases, while a modification can be made to compensate for the surface irregularity. For example, FIGS. 5-6 show a surface irregularity 42 that is a slight dip in the contour that is not reflected in the contour of the surface 24. To compensate for this while allowing the same length sliding indicator 26 to be used in both locations shown in FIGS. 5-6, the collar 26C1 defining the bore 26B receiving the sliding indicator 26 that makes contact with the surface irregularity 42 is made to have a lesser height than the collar 26C2 of the bore receiving the sliding indicator 26 that makes contact with the regular surface 40. In this way, because the indicator 26 contacting 42 will not be pressed into the bore 26B as much as the other indicator, it will still fill the proximal end of the bore 26B when the indicator has become properly aligned with the irregular contour. Thus, the differences by which the distal ends of the sliding indicators 26 extend from the surface 24 when they are aligned in conformity with the contours of the target tissue can be compensated for by inverse differences in the heights of the collars that receive the proximal ends of the indicators 26. It is further noted, that if a surface irregularity of the target tissue is in a location that corresponds to one or more locations of the anchors 22, the lengths by which the anchors extend from the surface 24 can be modified to account for the irregularity.

Figures 7A, 7B:
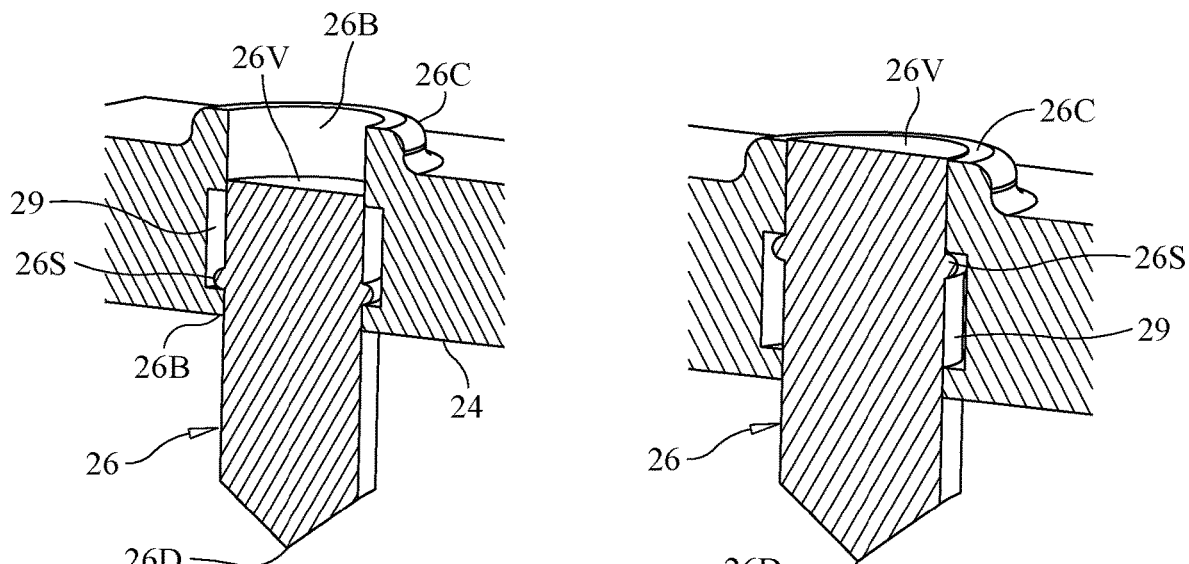
FIG. 7A is a longitudinal sectional view of a position indicator in an initial configuration, according to an embodiment of the present invention.
FIG. 7B is a longitudinal sectional view of the position indicator of FIG. 7A after the position indicator has been slid to its docking position.

FIG. 7A is a longitudinal sectional view of a position indicator 26 in an initial configuration. As previously noted, the position indicator 26 is initially positioned so that the distal tip 26D extends from the distal surface 24 of the main body of the device 10 by an amount that extends distally of a contour surface formed by the loci of the distal ends 22D of anchors 22 in three dimensional space. In this position, the proximal end/visual indicator 26V is not aligned with the surface of the collar 26C and would not be visible or visibly aligned when viewed by a surgeon. This would indicate that the device 10 has not yet been accurately docked. At least one stop 26S is formed on position indicator 26 that is restricted by the distal end of track 29 which prevents it from being slidable distally out of the distal surface 24 of the device 10. This also defines a position by which the position indicator 26 can extend maximally distally from the surface 24 and this is the preferred initial position of the position indicator 26 relative to the surface 24. Position indicator 26 may be frictionally fit relative to bore 26B so that the position indicator 26 maintains its position relative to the surface 24 until a pressing force is applied that is greater than the frictional force of the friction fitting. Alternatively or additionally, position indicator 26 could be biased (such as by spring biasing (not shown)) to the downward, initial position shown in FIG. 7A.

FIG. 7B is a longitudinal sectional view of the position indicator 26 of FIG. 7A after the position indicator has been slid to its docking position. That is, as the device is pressed against the target tissue, force is applied to the distal end 26D of the position indicator 26 causing it to slide into the main body of the device 10 until the distal tip 26D is at a locus that lies in the contour surface formed by the loci of the distal ends 22D of anchors 22 in three dimensional space. In this position, the proximal end/visual indicator 26V is flush with the surface of the collar 26C and would be visible/visibly aligned when viewed by a surgeon. This would indicate that the device 10 has been accurately docked. Note that this position may also coincide with the stop 26S abutting against the proximal end of track 29. The proximal end of track 29 prevents that stop 26S and therefore the position indicator 26 from being slidable proximally out of the device 10, and also prevents the distal end of the position indicator from being driven proximally beyond its location where it is in proper alignment with the distal ends 22D of the anchors on the imaginary contour surface that matches the contour surface of the target tissue. One or more stops 26S may be provided as one or more protrusions that slide in one or more slots 29, respectively. Alternatively, track 29 may be defined by a cylindrical bore of greater diameter than bore 26B and stop 26S could be one or more protrusions, or ring that protrudes outwardly from the main body of the indicator 26.

Figure 8A:
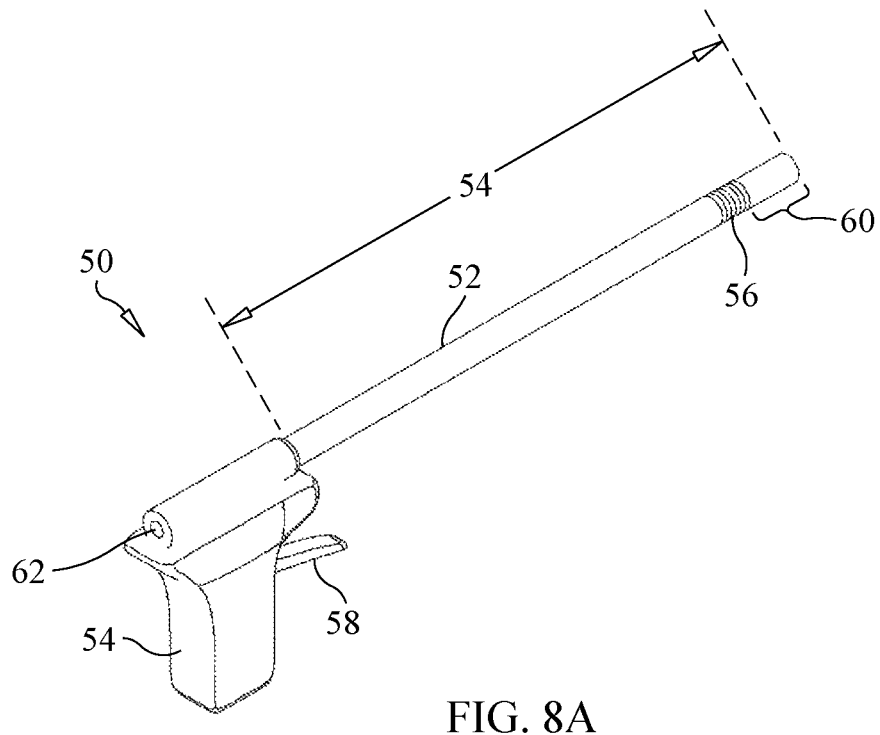
FIGS. 8A-8B are perspective views of an articulated sleeve tool that can be used in a minimally invasive procedure to deliver a device to target tissue, according to an embodiment of the present invention.
Figure 8B:
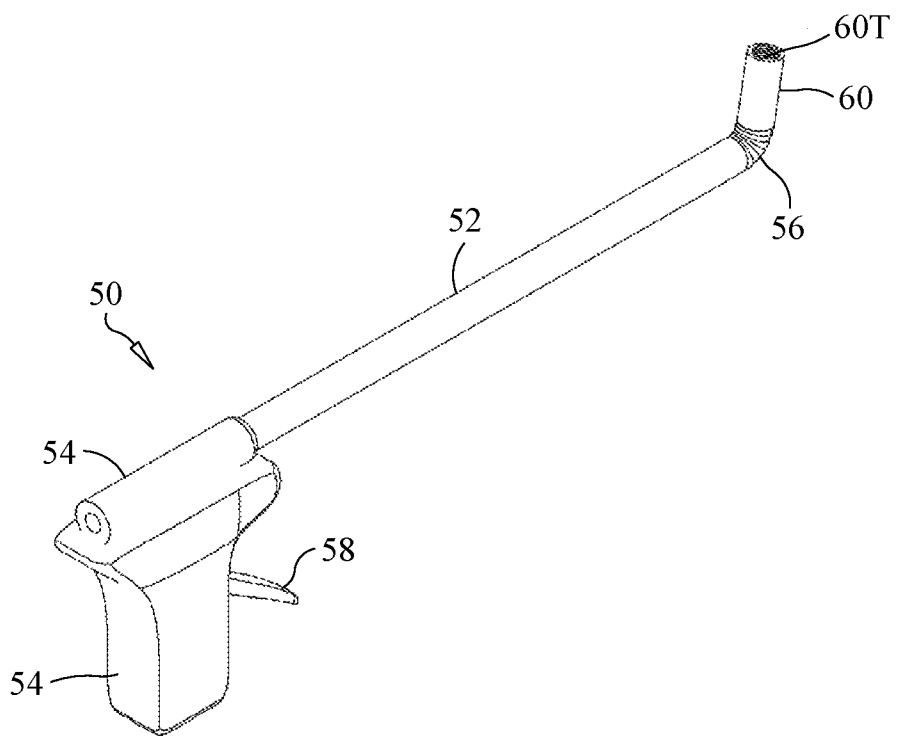

FIGS. 8A-8B are perspective views of an articulated sleeve tool 50 that can be used in a minimally invasive procedure to deliver device 10 to the target tissues. Tool 50 includes an elongate sleeve 52 which is a cannulated tube that extends distally from a handle 54 connected to or integral with a proximal end portion of the sleeve 52. Sleeve 52 has a length 54 from its distal end to the distal end of the handle that is greater than the length of a retractor through which the device 10 is to be delivered to the target tissues. This ensures that the handle 54 can be operated from a location proximal of the retractor even as the device 10 is placed into contact with the target tissues. Sleeve 52 further includes a joint 56 which can be articulated by operation of actuator 58 to angulate the distal end portion 60 relative to the sleeve portion that is proximal of the join 56. Distal end portion 60 may have a length of 10 mm to 25 mm, more preferably 15 mm to 20 mm. In one particular example, the length of distal end portion 60 was 15 mm.

The diameter of the annulus 62 of sleeve 52 is about equal to, or slightly larger than the outside diameter of optimal axis guide 20, so that the tool 50 can be removably attached to the device 10. The diameter of annulus 62 may be in the range from 3.2 mm to 4 mm, preferably 3.4 mm to 3.8 mm. In one particular example, the diameter of the annulus 62 was 3.4 mm. When the actuator 58 is in the resting position (unbiased), the sleeve 52 is biased toward the unarticulated or straight configuration shown in FIG. 8A.

Upon actuation of the actuator, such as by applying finger pressure to trigger 58 as illustrated FIG. 8B while squeezing handle 54, or by otherwise actuating an alternative form of actuator, that actuation biases the distal tip 60 about the articulating joint. As shown in FIG. 8B, the distal tip can be angulated to the longitudinal axis of the unbiased sleeve by an angle from about 0 to 90 degrees. Upon release or deactivation of the actuator 58, the distal tip 60 returns to the straight configuration (0 degrees) illustrated in FIG. 8A. The distal tip 60 is configured to be releasably attached to the device 10. In the embodiment shown in FIG. 8B, distal tip 60 is internally threaded with threads 60T that match threads 20T on the optimal axis guide 20 of device 10 (as well as other embodiments described herein, e.g., 10', 10"). Alternative methods of releasably attaching the sleeve tool 50 to the device 10 could be substituted using known expedients.

Figure 9:
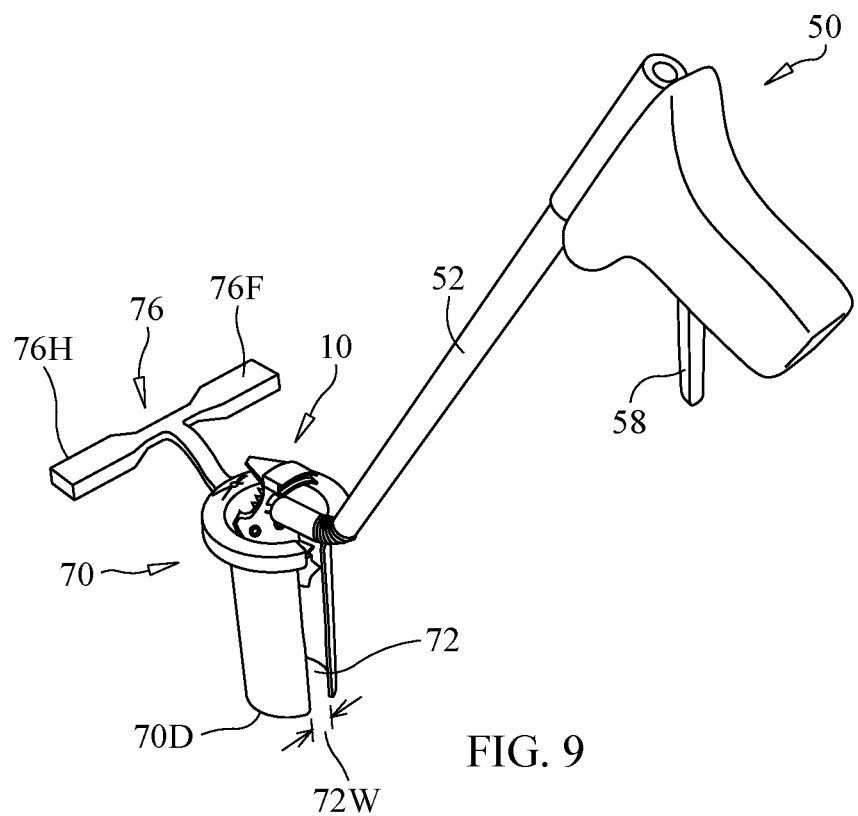
FIG. 9 illustrates use of tool to deliver a device through a retractor or access port to a vertebra of a patient in a minimally-invasive (MIS) surgical procedure, according to an embodiment of the present invention.

FIG. 9 illustrates use of tool 50 to deliver device 10 through a retractor or access port 70 to a vertebra of a patient in a minimally-invasive (MIS) surgical procedure, according to an embodiment of the present invention. The retractor may be a slotted access port 70 as shown. Further embodiments and details of a retractor that could be used are disclosed in detail in U.S. Pat. No. 10,524,831 titled "MIS Access Port and Methods of Using", which issued on Jan. 7, 2020 and which is incorporated herein, in its entirety, by reference thereto.

In carrying out such an MIS procedure, typically, an incision having a length in the range of about 15 mm to about 18 mm is made through the skin of a patient overlying the vertebra to be operated on and the fascia and other tissues underlying the skin are manipulated with tools to provide a minimally invasive opening to the vertebra 1 (surgical target location). Optionally, a K-wire or other guide can be first inserted through the opening made by the incision and then dilators of increasing diameter can be subsequently used to increase the size of the pathway leading to the surgical target location. Alternatively, the retractor/access port 70 can be installed without the use of a K wire or guide, for a posterior procedure.

The retractor 70 is inserted through the opening of the skin, with or without guidance by a guide, and installed so that a distal end 70D of the retractor 70 is in contact with the vertebra 1 and surrounds the target tissues (mainly bone) to which device 10 is to be placed in contact with.

Once the retractor 70 has been installed as described above, a connector 76 that is rigidly attached to or integral with retractor 70A can be used to connect the retractor to an interconnecting rod or linkage that is also connected to a stationary object, such as the operating table or other stationary object, so that the retractor is fixed relative to the stationary object. Connection to the stationary object can be made using either end 76H or 76F of the connector, at the preference of the surgeon. For example, the connection linkage may extend in a direction toward the head of the patient when connecting using 76H or the connection linkage may extend toward the feet of the patient when connecting using 76F.

Device 10 may be connected to tool 50 such as by turning the threads 60T of tool 50 over the threads 20T of the optimal axis guide 20. Once connected, actuator 58 is actuated to articulate the joint 56 so as to angle the distal tip portion 60 of the sleeve 52 relative to the longitudinal axis of the sleeve and the majority of the sleeve. This angulation also rotates the device 10 that is connected to the tip 60 so that the longest dimension of the device 10 can be generally aligned near the longitudinal axis of the port 70 so that the device 10 can be inserted through the port 70 with the smaller thickness and width dimensions extending transverse across the port annulus and the larger dimension (length) of the device 10 more aligned with the longitudinal axis of the port. This allows the device 10 to be delivered through the port 70 in an integral form, without requiring any disassembly to pass parts of the device 10 through the port. FIG. 9 illustrates the device 10 being passed through the port 70 where the wings of the device extend in the direction of the longitudinal axis of the port 70, such that the length dimension of the device is substantially aligned with the longitudinal axis of the port 70.

Figure 10:
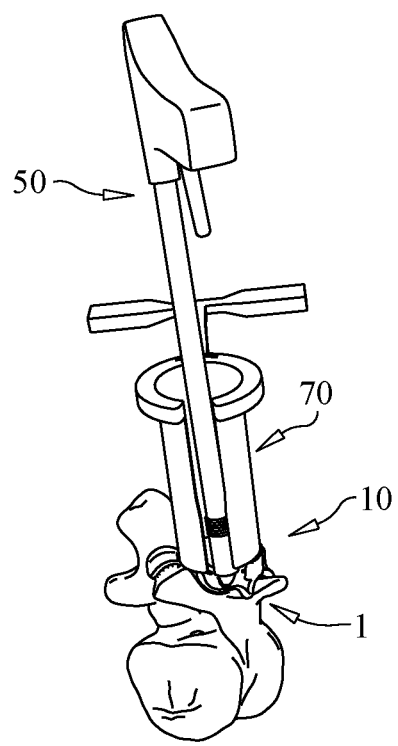
FIG. 10 illustrates the retractor of FIG. 9 having been docked on the device, according to an embodiment of the present invention.

The slot 72 that extends over then entire length of the retractor/port 70 has a width 72W that is greater than the outside diameter of the sleeve 52, thus allowing the sleeve 52 to slide within the slot as the device 10 is delivered through the port 70. As the device 10 is delivered to the distal end portion of the retractor 70, the retractor 70 is partially withdrawn to provide a gap between the distal end of the retractor 70 and the vertebra 1. This allows the device 10 to be delivered distally of the distal end of the retractor. While the device 10 is being so delivered, the surgeon will at the same time release pressure on the actuator 58 thereby allowing the sleeve tip 60 to return to the straight configuration shown in FIG. 8A, at the same time rotating the device 10 so that the surface 24 faces the target tissues. The retractor 70 is next docked on the device 10 by inserting portions of the distal end of the retractor into the arcuate slots 32 of retractor mounts 30. FIG. 10 illustrates the retractor 70 having been docked on the device 10. Either before or after this docking (preferably after), pressure is applied to the device to move it into the correct orientation in apposition with the target tissues, and this correct orientation can be visibly verified when the surgeon sees each of the visual indicators 26P that were described above. When the pressure to correctly orient the device 10 is applied after docking, pressure can be applied in whole through the retractor 70 itself, or in combination with pressure applied through tool 50 or other tool. The retractor 70, once docked, helps to maintain the device in contact with the target tissues and maintains an open visualization space that can be viewed from outside of the patient.

Figure 11:
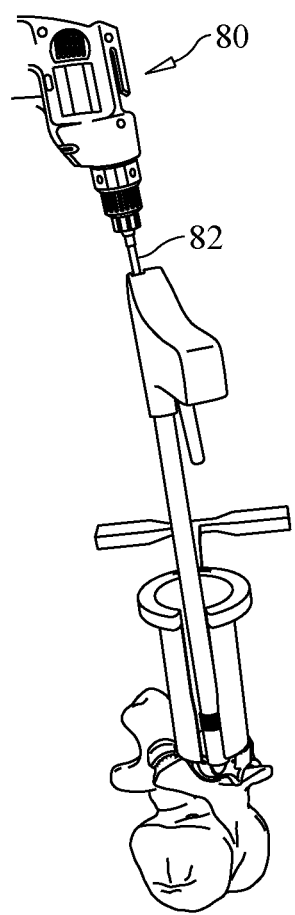
FIG. 11 illustrates a drill being used to drill target bone of a vertebra to create a pathway having an optimal axis along which a pedicle screw can be implanted, according to an embodiment of the present invention.
Figure 12:
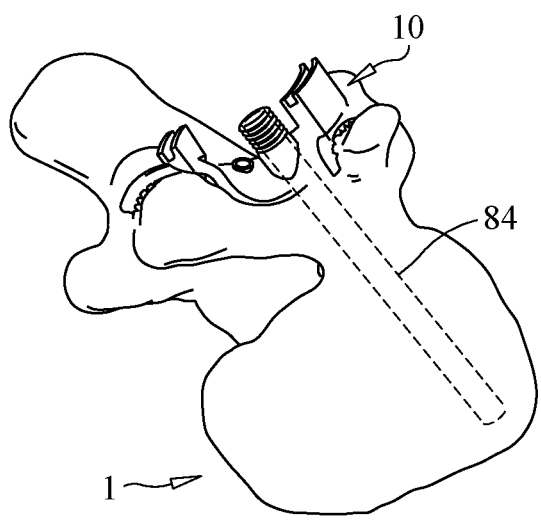
FIG. 12 illustrates the optimum pathway (in phantom lines) created by the drilling procedure illustrated in FIG. 11.

Once the device 10 has been correctly positioned in contact with the target tissues a drill 80 can be used to drill the target bone of the vertebra 1 to create a pathway having an optimal axis along which a pedicle screw can be implanted, as illustrated in FIG. 11. The drill bit 82 is maintained along the optical axis by the sleeve 52 and the sleeve 52 is maintained coaxially with the optimal axis by its connection to the optimal axis guide 20, which was designed to establish the optimum axis. FIG. 12 illustrates the optimum pathway 84 (in phantom lines) created by the drilling procedure described previously. For clarity, the retractor is not shown in FIG. 12, although it would be still in place even after completion of the drilling procedure.

After the drilling procedure, the retractor 70 can be slightly retracted to again provide a space between distal end 70D and the target tissues that is sufficient to allow the device 10 to again be rotated by articulation of the distal tip 60. In this way the device 10 can be withdrawn out of the port 70 and the patient, in the same or similar orientation that it was placed in during the initial delivery, so that the largest dimension of the device 10 is most aligned with the longitudinal axis of the port 70.

After removal of the device 10 from the port 70, a pedicle screw can be installed through the port 70 and torqued into the pathway 84 so that it is anchored to the vertebra along the optimal axis of implantation 84 as determined by the patient specific 3D modeling and established by the procedure described above. The implantation of the pedicle screw can be in conjunction with implantation of other hardware and or other procedures that are to be carried out during this MIS procedure.

Upon completion of the implantation of the pedicle screw and any other hardware and procedures included in this MIS surgery, the access port 70 is disconnected from its anchoring to a stationary object and then the access port 70 is removed and the patient is closed according to standard procedures.

Some of the features of patient anatomy, even when performing the same surgical procedure, may not always be present from patient to patient. Because the present invention provides patient-specific 3D planning, the resultant devices that are manufactured differ in regard to each patient. Not only will the contour of the distal surface 24 (and the contour mapped out by distal ends of anchors 22 and indicators 26) of device 10 vary from patient to patient, but in some instances, the device may need to be designed to contact different features from patient to patient. This could be due to prior surgical revisions, deformity, injury, or other reason that would cause the anatomy to be significantly different from normal. This can also be the result when surgical procedures are to be carried out at different levels of the spine.

Figure 13:
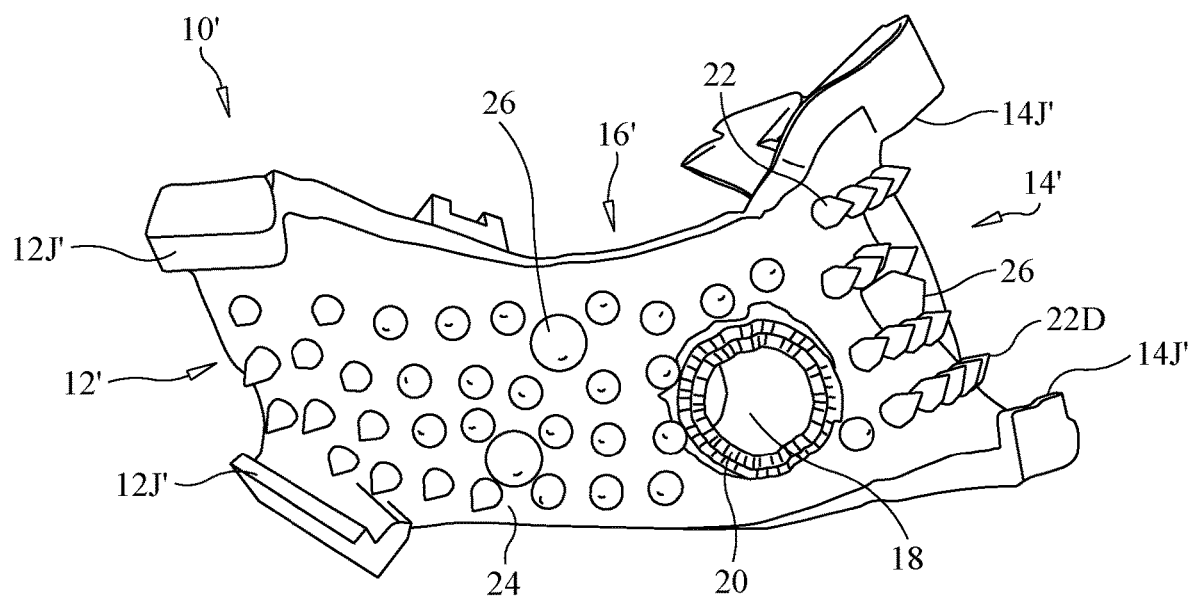
FIG. 13 shows a distal surface of a guide device according to another embodiment of the present invention.

FIG. 13 shows the underside (distal surface) of guide device 10' according to another embodiment of the present invention. The guide 10' of FIG. 13 is a patient-specific 3D surgical planning navigational guide that is designed specifically to fit anatomical contours of a specific vertebra of a specific patient, and which can be used in minimally invasive spinal surgery. In the embodiment shown, the guide 10' is designed for a specific T4 vertebra. Although this embodiment is primarily provided for specific design according to principles described herein for any specific vertebra of a specific patient in the cervical or thoracic spine, it could also be used for specific design to fit a specific vertebra of a lumbar spine of a specific patient. FIG. 13 shows the contoured surfaces 24 of portions 12, 14' and 16 that are configured to be placed to conform in apposition to specific anatomic features of a specific patient. Anchors 22 extend from the apposition surfaces 24 and are configured to contact the target tissues of the anatomy and prevent the device 10' from sliding relative to the anatomy to which it is contacted, once the device has been properly oriented. The anchors 22 may be the same as those described with regard to FIGS. 1 and 3, for example. The free (pointed) ends 22D of the anchors extend from the contoured surfaces 24 by distances that maintain the matching contour to the anatomical surface that they are to contact. Thus, for example, if a 3D topological map of the points 22D of anchors 22 is plotted, the topological map conforms to the contours of the anatomical features that the points 22D are to be placed in contact with. The undersurface 24 from which the anchors 22 extend may also be contoured (but not necessarily) to match the contours of the anatomical features that the device 10' is to be placed into contact with via anchors 22.

Figure 14:
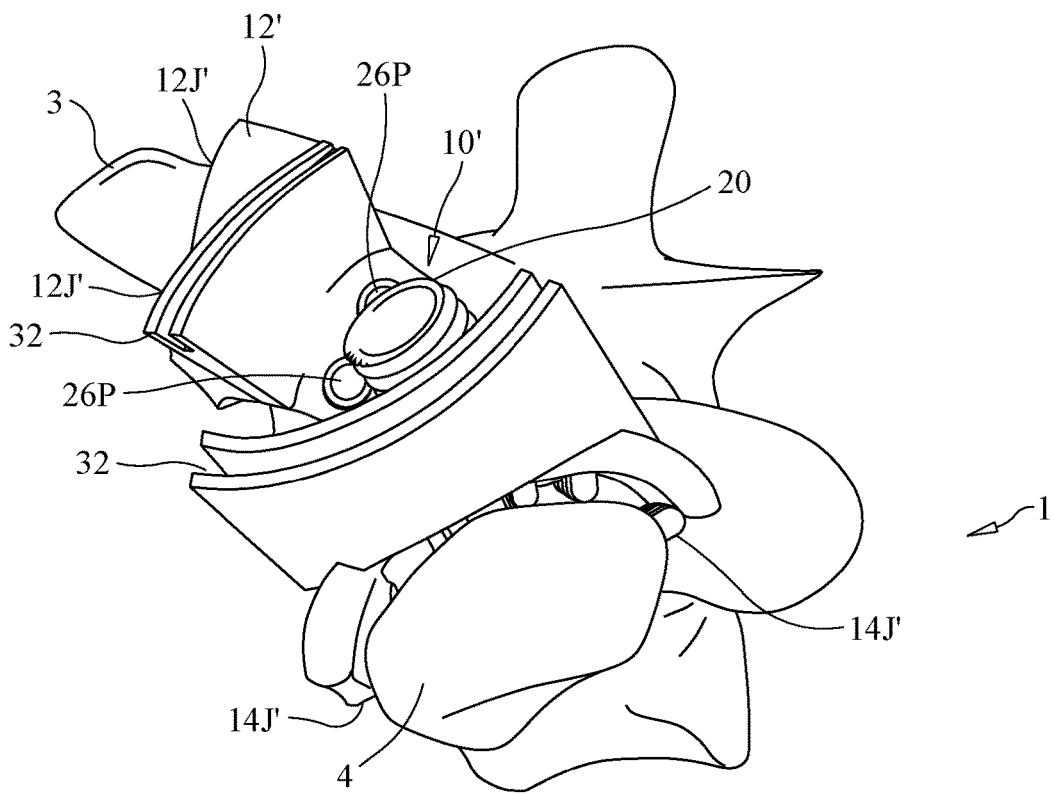
FIG. 14 illustrates device of FIG. 13 having been properly docked in apposition against a vertebra of a patient.

A number of position indicators 26 are provided in device 10' in the same manner and which may have the same characteristics as those described with regard to device 10 above. FIG. 13 illustrates the sliding indicators 26 extending out of the surface 24 by distances which place there free distal ends in alignment with a contour that matches the anatomy to be contacted, along with the free distal ends 22D of the anchors 22. FIG. 13 shows the indicators 26 in the positions that they would assume when slid to their final positions indicating that the device has been correctly positioned and docked to the target tissues. FIG. 14 shows one and a partial one of the indicators 26P that show that the device 10' has been correctly positioned (docked) in contact with the target tissues of the vertebra 1.

Device 10' may also include jaws that oppose one another and have faces that face towards one another and are configured to contact the anatomy in opposition to one another to grossly position the anatomy that they contact to prevent sliding of the device 10' relative to the anatomy. FIG. 13 shows jaws 12J' in opposition to one another, configured to contact surfaces of the spinous process 3 to prevent sliding of the wing 12' in directions along which the jaws 12J' oppose one another. Like device 10, device 10' may include jaws 14J configured to apply opposing contact to the transverse process 4 to prevent sliding along directions in which the jaws 14J oppose one another. Optimal axis guide 20 is an integral part of the device that extends and defines bore 18 along an optimal trajectory for drilling to provide an optimum pathway to implant a pedicle screw.

When the device 10' is installed on the anatomy that it is designed to fit over, the free ends of the sliding indicators 26 contact the anatomical structures (e.g., bone surface) first, as they extend further out that the anchors 22 when in the initial configuration. As the device 10' is pushed further against the anatomy, the sliding indicators 26 slide further into the device 10' until they conform with the ends 22D so that they match the contour of the anatomical feature that they are contacting. Once the ends 22D contact the anatomy and cannot be pushed any further into the bone, the sliding indicators 26 also cannot be slid any further relative to the body of the device 10' and the visual indicators 26P become visible to the surgeon viewing the proximal side of the device 10'.

FIG. 14 illustrates device 10' having been properly docked in apposition against a vertebra 1 of a patient. More specifically, jaws 14J' contact against the transverse process 4 in opposite directions and prevent the device 10'/wing 14' from sliding across the transverse process 6 (in left-right directions shown in FIG. 14). Jaws 12J' contact against the spinous process 3 and prevent the device 10'/wing 12' from sliding across the spinous process 3 (in up-down directions shown in FIG. 14). The jaws 12J', 14J' also help to orient the device 10' in the correct two-dimensional position relative to the patient's bones. For correct three-dimensional placement and docking, the device 10' is pressed against the target surface forcing the anchors 22 into contact with the target contours. This also drives the position indicators 26 into conformity with the conforming surfaces defined by the ends of the anchors 22 and indicators 26 as they contact the target surface. Once completely docked, the proximal ends 26P of the indicators 26 show visibly as they fill the indicator bores 26B, as partially shown in FIG. 14. The proximal ends 26P may optionally be colored with a color that sharply contrasts with the color of the device 10/indicator bore 26B ring, so that they can be easily seen. Proximal ends 26P are not visible until the device 10 has been properly contacted and oriented to the target contact surface in a three-dimensional relationship. Once properly placed (properly docked), the optimal axis guide 20 has a longitudinal axis passing through bore 18 that defines the optimal trajectory along which to drill the bone to provide the optimum delivery pathway for installation of a pedicle screw.

In addition to indicating an optimal trajectory, it is desirable to efficiently choose target tissues of the patient anatomy against which the device 10, 10' is to be contacted/docked. One constraint is keeping the overall dimensions of the device small enough so that they can be delivered through the retractor/port 70. The devices described herein can be delivered, each in whole, as an integral device, so that no disassembly and reassembly is required prior to and after delivery, respectively. The diameter of the port of retractor 70 through which the device 10, 10' is to be delivered may vary depending upon the level of the spine that the target vertebra is located in, but may range from about 20 mm to 30 mm, typically about 22 mm to 28 mm, preferably about 24 mm to 26 mm. The limiting factors for passing device 10, 10' include the width and depth dimensions of the device 10, 10', as the length can be oriented in the direction of the longitudinal axis of the port. Maximum dimensions of a device 10, 10' that can be successfully inserted through a port are 25 mm mm width 110 and 25 mm mm depth 112. Maximum length 114 is typically no greater than 65 mm. In one specific example of device 10, length 114 was 40 mm, width 110 was 15 mm and depth 112 was 14 mm. In one specific example of device 10', length 114 was 32 mm, width 110 was 18 mm and depth 112 was 14 mm.

Figure 15:
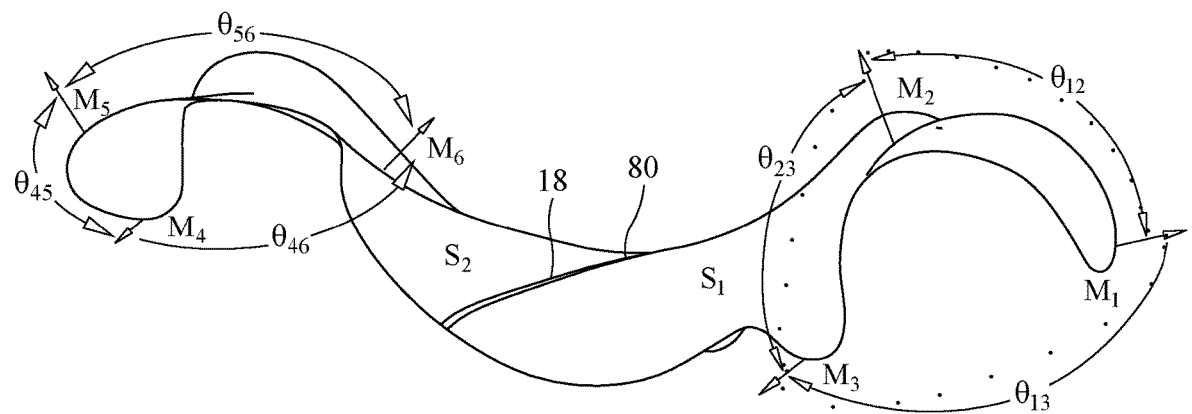
FIGS. 15 and 16 show maps of the surfaces of target tissue used in designing devices for use in the thoracolumbar and/or cervical spine according to an embodiment of the present invention.
Figure 16:
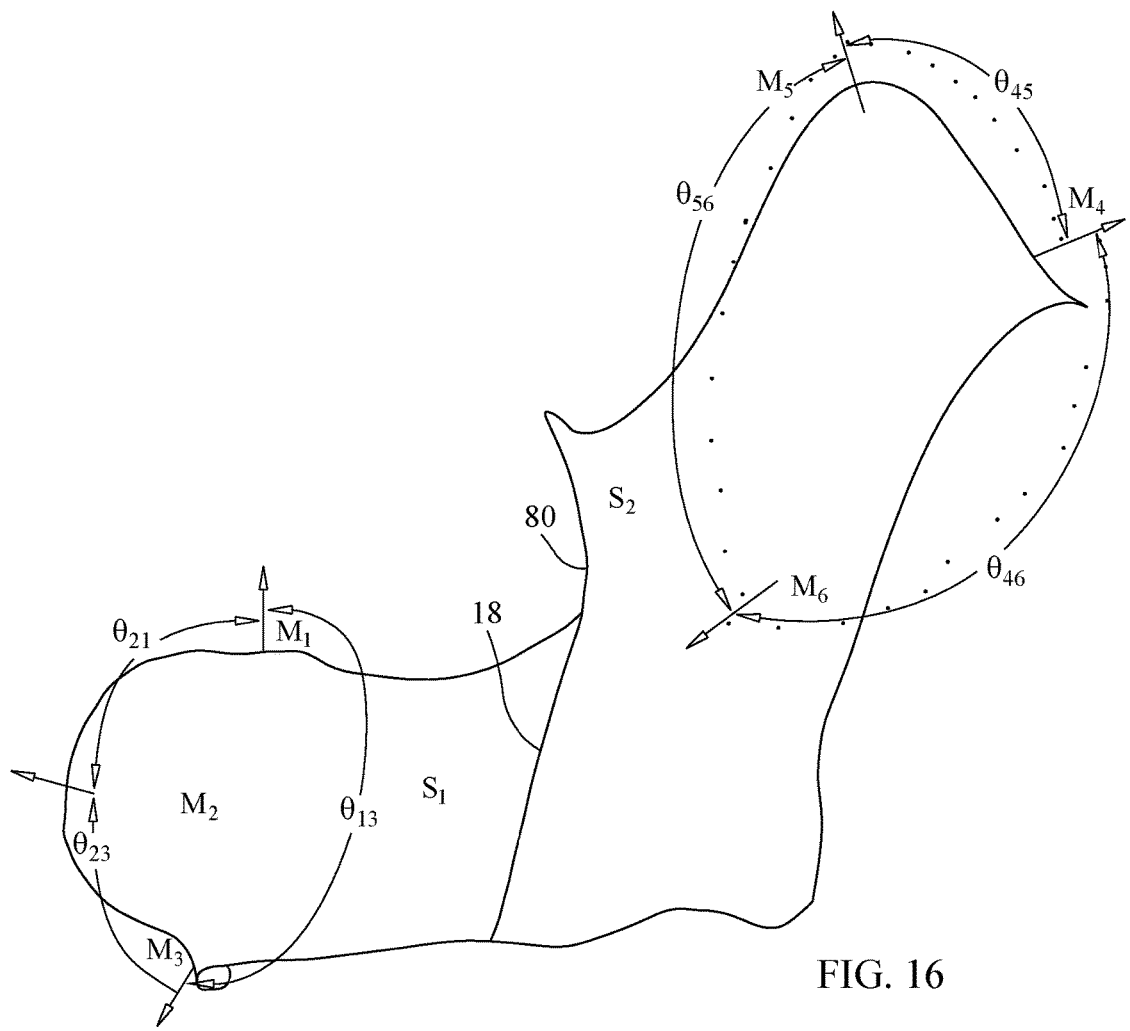

Within these maximum dimensions, anchors 22 extending from the surface 24 of device 10, 10' are located so that they contact the matching contour patient anatomy in a way to ensure stability of the docking of the device 10, 10' on the target patient anatomy. Once the location of the optimal trajectory and thus the location of where bore 18 will be drilled having the optimal trajectory, the target tissue of the patient is divided along a line or plane parallel to the sagittal plane. FIGS. 15 and 16 show maps of the surfaces of target tissue used in designing device 10 of FIG. 1 and device 10' of FIG. 14, respectively, on which the dividing line 80 has been indicated to pass through the center of the locus of bore 18 and to be parallel to the sagittal plane. From this, three points are selected on the surface of each side of the dividing line/plane 80, for a total of six point locations.

The points of contact ($M_1$, $M_2$, $M_3$, $M_4$, $M_5$, $M_6$) are selected to meet the following conditions: (1) each three of these points are located on one side of the plane 80 that divides the surface of contact into two surfaces through the planned pedicle screw entry point (i.e., bore 18); and (2) by defining $\theta_{ij}$ as the angle formed by any two normal vectors to the surface 24 of the device 10, 10' respectively at two different points $M_i$ and $M_j$, both on the same side $S_1$ or $S_2$, then $\cos \theta_{ij} \leq 0$ where $i \neq j$ and i, j=1, 2 . . . 6.

Once these locations have been selected, then the device 10, 10' is to have features that make contact at at least these predefined six contact points. Thus, anchors 22, indicators 26 and/or jaws 12J, 14J, 12J', 14J' may be configured to make contact with various of the preselected contact points. Therefore normal vectors defined coaxially with the anchors 22 or indicators 26 and vectors normal to an jaw contact surfaces will meet the conditions (1) and (2) above. Meeting these constraints will ensure that at least the minimum amount of curvature of the target tissue surfaces to be contacted will have been met to define a unique proper position of the device 10, 10' that is still relatively easy to orient the device 10, 10' to.

Figure 17:
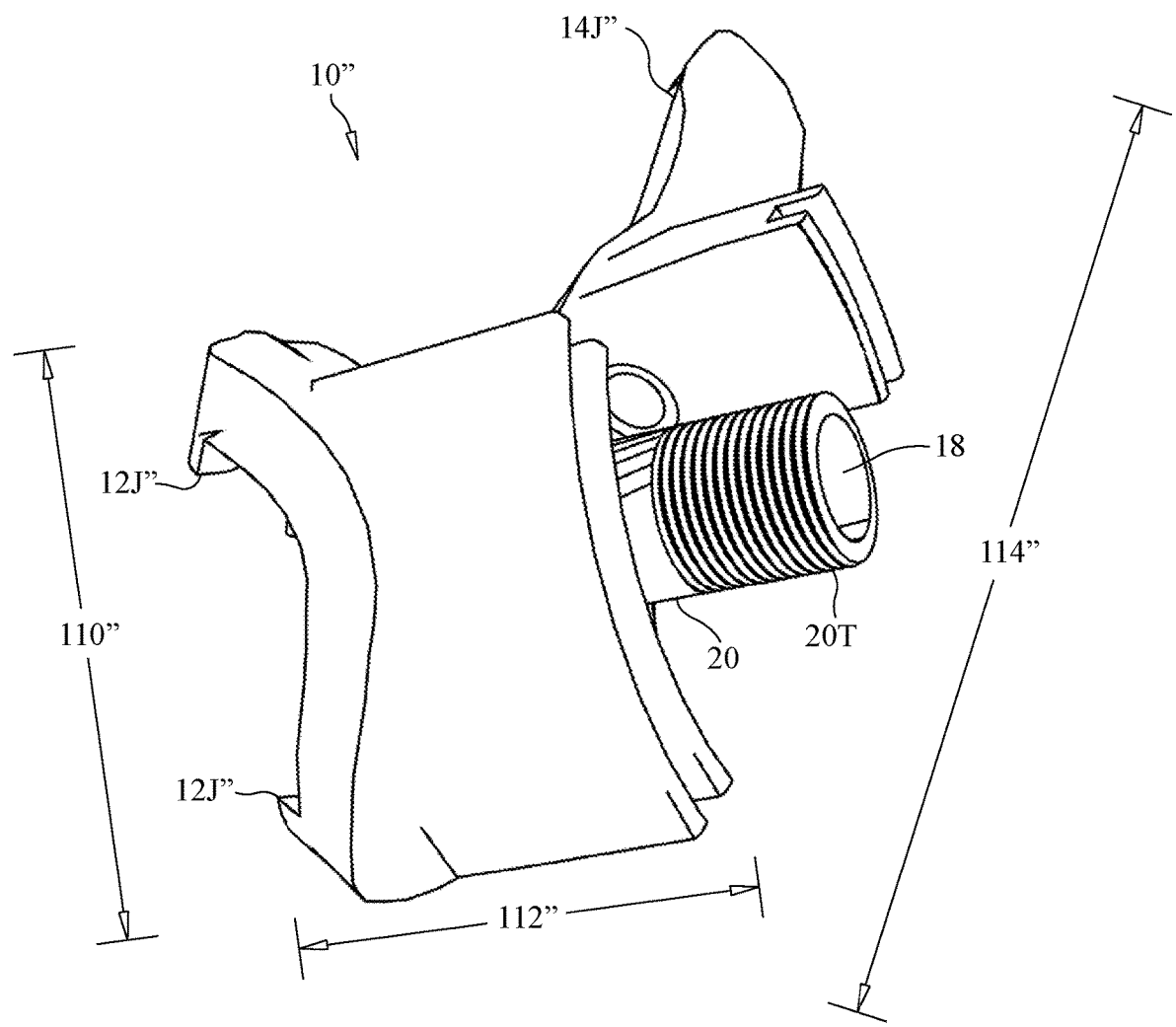
FIG. 17 is a perspective illustration from the proximal side of a navigational guide device according to another embodiment of the present invention.
Figure 18:
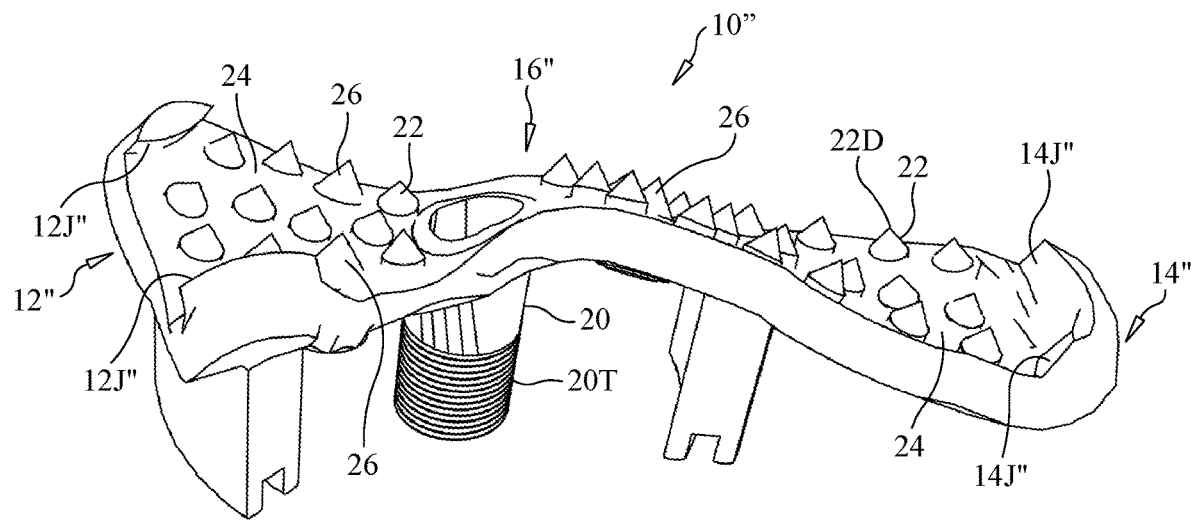
FIG. 18 is a perspective illustration from the distal side showing the underside (distal surface) of the navigational guide device of FIG. 17.

FIG. 17 is a perspective illustration from the proximal side and FIG. 18 is a perspective illustration from the distal side showing the underside (distal surface) of a navigational guide device 10" according to an embodiment of the present invention. While the embodiments 10 and 10' are designed to fit portions of specific vertebrae in the cervical or thoracolumbar spine, device 10" is designed to fit a portion of a specific S1 vertebra 1 in the sacrum of a specific patient. Reference numerals that are the same as in previous embodiments described may not be described here, as they can be the same as described above.

The contoured surfaces 24 of portions 12", 14" and 16" are configured to be placed to conform in apposition to specific anatomic features of a specific S1 vertebra of a specific patient. Anchors 22 extend from the apposition surfaces 24 and are configured to contact the target tissues of the anatomy and prevent the device 10" from sliding relative to the anatomy to which it is contacted, once the device 10" has been properly oriented. The anchors 22 may be the same as those described with regard to FIGS. 1 and 3, for example. The free (pointed) ends 22D of the anchors extend from the contoured surfaces 24 by distances that maintain the matching contour to the anatomical surface that they are to contact. Thus, for example, if a 3D topological map of the points 22D of anchors 22 is plotted, the topological map conforms to the contours of the anatomical features that the points 22D are to be placed in contact with. The undersurface 24 from which the anchors 22 extend may also be contoured (but not necessarily) to match the contours of the anatomical features that the device 10" is to be placed into contact with via anchors 22.

Figure 19:
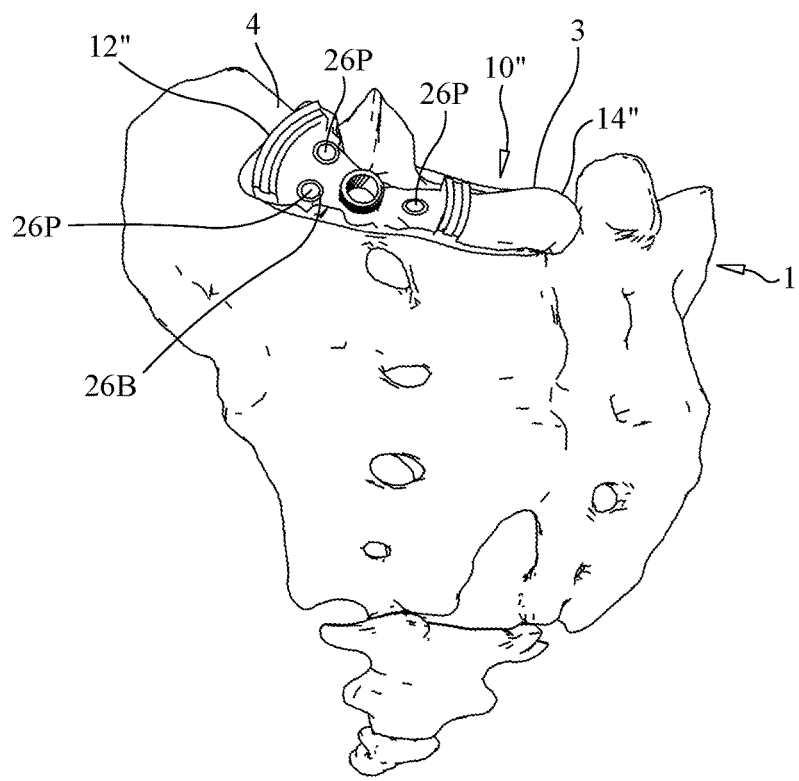
FIG. 19 shows the device of FIGS. 17-18 docked on a specific S1 vertebra, according to an embodiment of the present invention.

A number of position indicators 26 are provided in device 10" in the same manner and which may have the same characteristics as those described with regard to device 10 above. FIG. 18 illustrates the sliding indicators 26 extending out of the surface 24 by distances which place the free distal ends thereof in alignment with a contour that matches the anatomy to be contacted, along with the free distal ends 22D of the anchors 22. FIG. 18 shows the indicators 26 in the positions that they would assume when slid to their final positions indicating that the device has been correctly positioned and docked to the target tissues. FIG. 19 shows the proximal ends 26P of indicators 26 being visible to indicate that the device 10" has been correctly positioned (docked) in contact with the target tissues of the S1 vertebra 1.

Device 10" may also include jaws that oppose one another and have faces that face towards one another and are configured to contact the anatomy in opposition to one another to grossly position the anatomy that they contact to prevent sliding of the device 10" relative to the anatomy. FIG. 18 shows jaws 12J" in opposition to one another, configured to contact surfaces of the transverse process 4 of the S1 vertebra 3 to prevent sliding of the wing 12" in directions along which the jaws 12J" oppose one another. Like device 10, device 10" may include jaws 14J" configured to apply opposing contact to the spinous process 3 of the specific S1 vertebra 1 to prevent sliding along directions in which the jaws 14J" oppose one another. Optimal axis guide 20 is an integral part of the device 10" that extends and defines bore 18 along an optimal trajectory for drilling to provide an optimum pathway to implant a sacral screw.

When the device 10" is installed on the anatomy of the S1 vertebra that it is designed to fit over, the free ends of the sliding indicators 26 contact the anatomical structures (e.g., bone surface) first, as they extend further out than the anchors 22 when in the initial configuration. As the device 10" is pushed further against the anatomy, the sliding indicators 26 slide further into the device 10" until they conform with the ends 22D so that they match the contour of the anatomical feature that they are contacting. Once the ends 22D contact the anatomy and cannot be pushed any further into the bone, the sliding indicators 26 also cannot be slid any further relative to the body of the device 10" and the visual indicators 26P become visible to the surgeon viewing the proximal side of the device 10".

FIG. 19 illustrates device 10" having been properly docked in apposition against an S1 vertebra 1 of a specific patient. More specifically, jaws 12J" contact against the transverse process 4 in opposite directions and prevent the device 10"/wing 12" from sliding across the transverse process 4 (better shown in FIG. 22). Jaws 14J" contact against the spinous process 3 and prevent the device 10"/wing 14" from sliding across the spinous process 3. The jaws 12J", 14J" also help to orient the device 10" in the correct two-dimensional position relative to the S1 vertebra 1. For correct three-dimensional placement and docking, the device 10" is pressed against the target surface forcing the anchors 22 into contact with the target contours. This also drives the position indicators 26 into conformity with the conforming surfaces defined by the ends of the anchors 22 and indicators 26 as they contact the target surface of the S1 vertebra 1. Once completely docked, the proximal ends 26P of the indicators 26 show visibly as they fill the indicator bores 26B, as shown in FIG. 19. The proximal ends 26P may optionally be colored with a color that sharply contrasts with the color of the device 10"/indicator bore 26B ring, so that they can be easily seen. Proximal ends 26P are not visible until the device 10" has been properly contacted and oriented to the target contact surface in a three-dimensional relationship. Once properly placed (properly docked), the optimal axis guide 20 has a longitudinal axis passing through bore 18 that defines the optimal trajectory along which to drill the bone to provide the optimum delivery pathway for installation of a pedicle screw.

Guides 10, 10', 10" as described herein may be disposable templates, and may be manufactured from PEEK (polyether ether ketone) or other biocompatible polymers, for example.

Guides 10, 10', 10" may be produced by additive manufacturing, such as 3D printing, or any of the other techniques described above. Guides 10, 10' are individually designed to match the anatomy (e.g., bone surface anatomy) obtained from computed tomography images or other 3D visualization technique of a particular patient. Surgical procedures can be pre-operatively planned by computer-aided technologies, and the resulting patient-specific guides will then allow the surgeon to accurately replicate the planned operations.

In the embodiments described above, a surgeon may pre-operatively indicate an optimal screw trajectory and then the patient-specific guide 10, 10' is designed to mechanically constrain the drill, and consequently the pedicle screw/sacral screw, to follow that trajectory. As noted, the present invention is not limited to guiding the optimal trajectory of a pedicle screw or sacral screw, as many other types of MIS surgeries may be planned and facilitated by the present invention.

Like the previously described embodiments, tool 50 may be used to deliver device 10" through a retractor or access port 70. In this case the tool 50 and retractor 70 may be used for delivery of device 10" to an S1 vertebra of a specific patient in a minimally-invasive (MIS) surgical procedure, according to an embodiment of the present invention.

In carrying out such an MIS procedure, typically, an incision having a length in the range of about 15 mm to about 18 mm is made through the skin of a patient overlying the S1 vertebra to be operated on and the fascia and other tissues underlying the skin are manipulated with tools to provide a minimally invasive opening to the S1 vertebra 1 (surgical target location). It is noted that the underlying tissues beneath the incision and above the S1 vertebra will typically have significantly less thickness than the thickness of underlying tissues encountered with an MIS procedure for installing a device 10 or 10' on target tissue of a vertebra in the cervical or thoracolumbar spine. Optionally, a K-wire or other guide can be first inserted through the opening made by the incision and then dilators of increasing diameter can be subsequently used to increase the size of the pathway leading to the surgical target location. Alternatively, the retractor/access port 70 can be installed without the use of a K wire or guide, for a posterior procedure.

The retractor 70 is inserted through the opening of the skin, with or without guidance by a guide, and installed so that a distal end 70D of the retractor 70 is in contact with the S1 vertebra 1 and surrounds the target tissues (mainly bone) to which device 10a' is to be placed in contact with.

Once the retractor 70 has been installed as described above, a connector 76 that is rigidly attached to or integral with retractor 70 can be used to connect the retractor to an interconnecting rod or linkage that is also connected to a stationary object, such as the operating table or other stationary object, so that the retractor is fixed relative to the stationary object. Connection to the stationary object can be made using either end 76H or 76F of the connector, at the preference of the surgeon. For example, the connection linkage may extend in a direction toward the head of the patient when connecting using 76H or the connection linkage may extend toward the feet of the patient when connecting using 76F.

Figure 20:
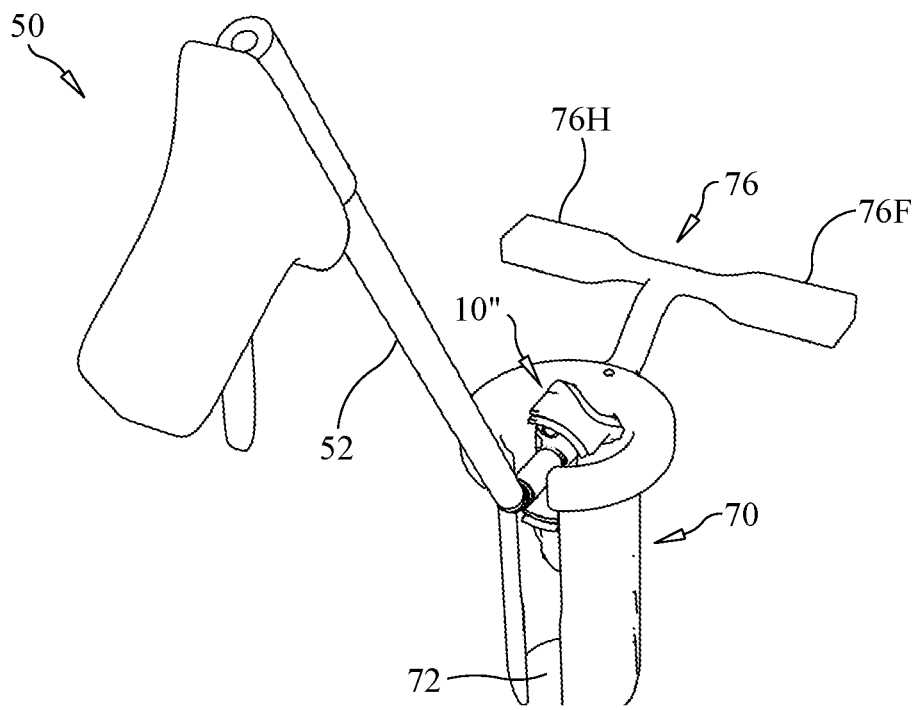
FIG. 20 shows insertion of a device into a retractor using a tool according to an embodiment of the present invention.

Device 10" may be connected to tool 50 such as by turning the threads 60T of tool 50 over the threads 20T of the optimal axis guide 20. Once connected, actuator 58 is actuated to articulate the joint 56 so as to angle the distal tip portion 60 of the sleeve 52 relative to the longitudinal axis of the sleeve and the majority of the sleeve. This angulation also rotates the device 10" that is connected to the tip 60 so that the longest dimension of the device 10" can be generally aligned near the longitudinal axis of the port 70 so that the device 10" can be inserted through the port 70 with the smaller thickness and width dimensions extending transverse across the port annulus and the larger dimension (length) of the device 10" more aligned with the longitudinal axis of the port, as illustrated in FIG. 20. This allows the device 10" to be delivered through the port 70 in an integral form, without requiring any disassembly to pass parts of the device 10" through the port 70. FIG. 20 illustrates the device 10" being passed through the port 70 where the wings of the device extend in the direction of the longitudinal axis of the port 70, such that the length dimension of the device is substantially aligned with the longitudinal axis of the port 70.

Figure 21:
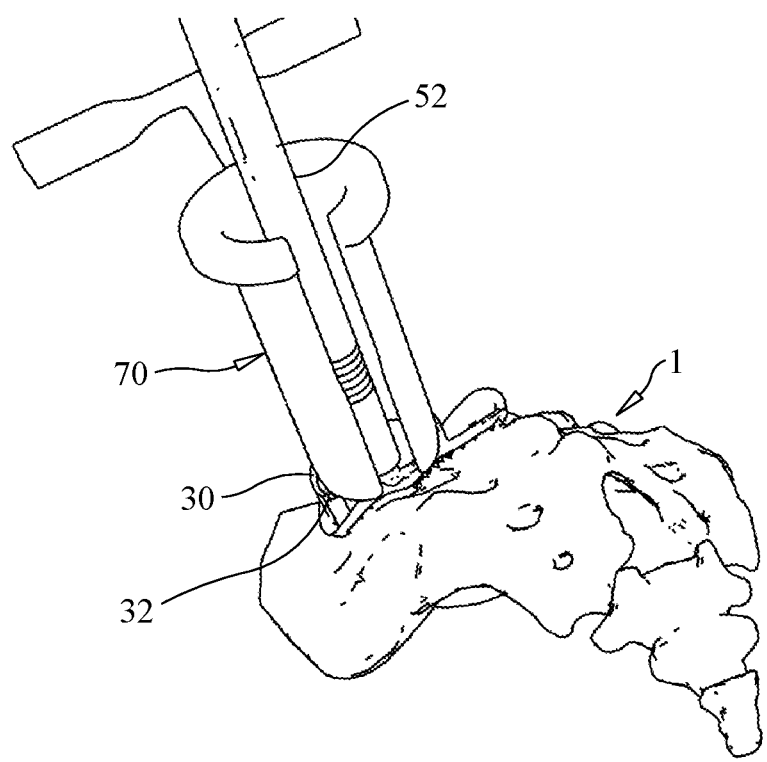
FIG. 21 shows a retractor mounted on the device of FIG. 20, the device contacted to a specific S1 vertebra according to an embodiment of the present invention.

The slot 72 allows the sleeve 52 to slide within the slot as the device 10" is delivered through the port 70. As the device 10" is delivered to the distal end portion of the retractor 70, the retractor 70 is partially withdrawn to provide a gap between the distal end of the retractor 70 and the S1 vertebra 1. This allows the device 10" to be delivered distally of the distal end of the retractor 70. While the device 10" is being so delivered, the surgeon will at the same time release pressure on the actuator 58 thereby allowing the sleeve tip 60 to return to the straight configuration shown in FIG. 8A (also in FIG. 21), at the same time rotating the device 10" so that the surface 24 faces the target tissues of the S1 vertebra. The retractor 70 is next docked on the device 10" by inserting portions of the distal end of the retractor 70 into the arcuate slots 32 of retractor mounts 30. FIG. 21 illustrates the retractor 70 having been docked on the device 10". Either before or after this docking (preferably after), pressure is applied to the device to move it into the correct orientation in apposition with the target tissues, and this correct orientation can be visibly verified when the surgeon sees each of the visual indicators 26P that were described above. When the pressure to correctly orient the device 10" is applied after docking, pressure can be applied in whole through the retractor 70 itself, or in combination with pressure applied through tool 50 or other tool. The retractor 70, once docked, helps to maintain the device in contact with the target tissues and maintains an open visualization space that can be viewed from outside of the patient.

Figure 22:
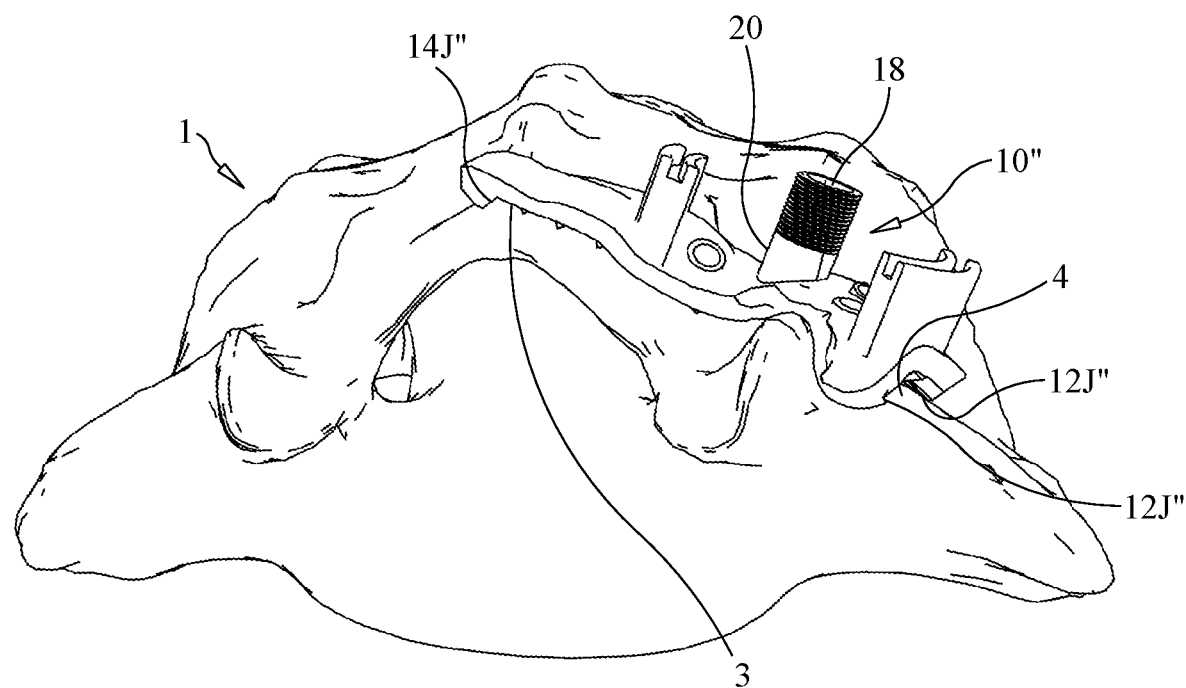
FIG. 22 illustrates docking of the device of FIGS. 17-18 to a specific S1 vertebra and illustrates contact of the jaws to specified processes.
Figure 23:
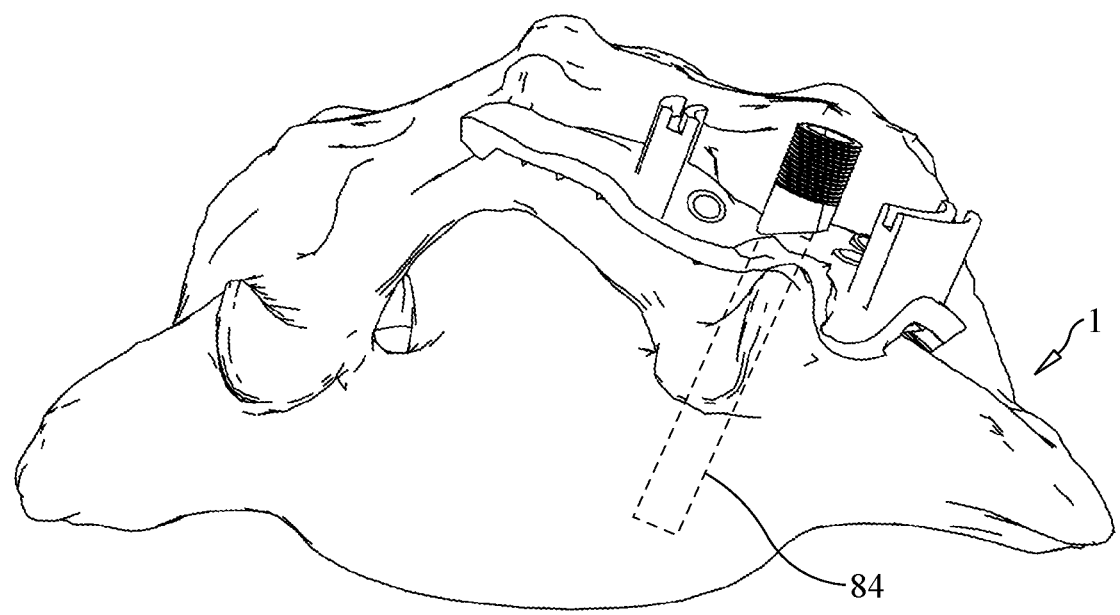
FIG. 23 illustrates an optimum pathway (in phantom lines) created by a drilling procedure according to an embodiment of the present invention.

Once the device 10" has been correctly positioned in contact with the target tissues a drill 80 can be used to drill the target bone of the S1 vertebra 1, in the same manner described above with regard to FIG. 11, to create a pathway having an optimal axis along which a sacral screw can be implanted, as illustrated in FIG. 23. The drill bit 82 is maintained along the optical axis by the sleeve 52 and the sleeve 52 is maintained coaxially with the optimal axis by its connection to the optimal axis guide 20, which was designed to establish the optimum axis. FIG. 22 illustrates device 10" having been accurately docked against the target tissues of the S1 vertebra 1. The retractor 70 is not shown here so as to simply the view and focus on the proper fitting of the device 10" to the contours of the target tissues. As noted because of the complex topology of the target tissues that are contacted, and the matching contours provided to the device 10", there is only one orientation in which the device 10" can be placed to properly contact and fit against the target tissues. FIG. 23 illustrates the optimum pathway 84 (in phantom lines) created by the drilling procedure described previously. For clarity, the retractor is not shown in FIG. 23, although it would be still in place even after completion of the drilling procedure.

After the drilling procedure, the retractor 70 can be slightly retracted to again provide a space between distal end 70D and the target tissues that is sufficient to allow the device 10" to again be rotated by articulation of the distal tip 60. In this way the device 10" can be withdrawn out of the port 70 and the patient, in the same or similar orientation that it was placed in during the initial delivery, so that the largest dimension of the device 10" is most aligned with the longitudinal axis of the port 70.

After removal of the device 10" from the port 70, a sacral screw can be installed through the port 70 and torqued into the pathway 84 so that it is anchored to the S1 vertebra 1 along the optimal axis of implantation 84 as determined by the patient specific 3D modeling and established by the procedure described above. The implantation of the sacral screw can be in conjunction with implantation of other hardware and or other procedures that are to be carried out during this MIS procedure.

Upon completion of the implantation of the sacral screw and any other hardware and procedures included in this MIS surgery, the access port 70 is disconnected from its anchoring to a stationary object and then the access port 70 is removed and the patient is closed according to standard procedures.

Like noted above with regard to devices 10 and 10', in addition to indicating an optimal trajectory, it is desirable to efficiently choose target tissues of the patient anatomy against which the device 10" is to be contacted/docked. One constraint is keeping the overall dimensions of the device small enough so that they can be delivered through the retractor/port 70. The devices described herein can be delivered, each in whole, as an integral device, so that no disassembly and reassembly is required prior to and after delivery, respectively. The diameter of the port of retractor 70 through which the device 10, 10' is to be delivered may vary depending upon the level of the spine that the target vertebra is located in, but may range from about 20 mm to 30 mm, typically about 22 mm to 28 mm, preferably about 24 mm to 26 mm. The limiting factors for passing device 10, 10' include the width and depth dimensions of the device 10, 10', as the length can be oriented in the direction of the longitudinal axis of the port. Maximum dimensions of a device 10" that can be successfully inserted through a port are 25 mm width 110" and 25 mm depth 112". Maximum length 114" is typically no greater than 65 mm. In one specific example of device 10", length 114" was 45 mm, width 110" was 17 mm and depth 112" was 14 mm.

Figure 24:
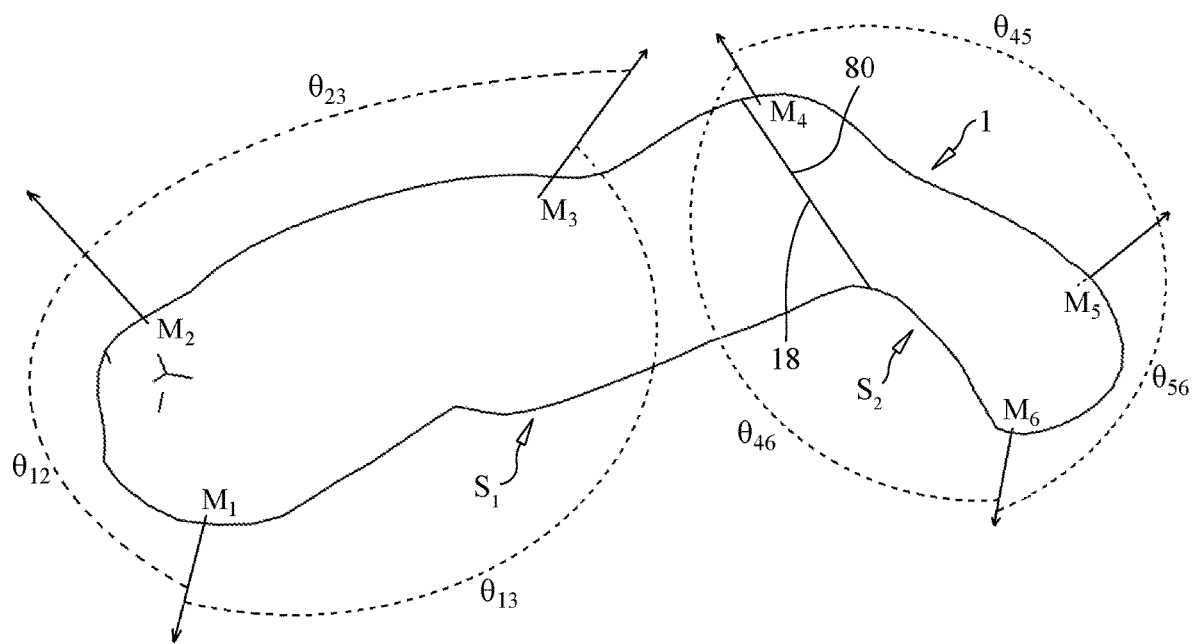
FIG. 24 shows an example of a map of surfaces of target tissue on an S1 vertebra of a specific patient that can be used in designing a device of FIG. 17, according to an embodiment of the present invention.

Within these maximum dimensions, anchors 22 extending from the surface 24 of device 10" are located so that they contact the matching contour patient anatomy in a way to ensure stability of the docking of the device 10" on the target patient anatomy. Once the location of the optimal trajectory and thus the location of where bore 18 will be drilled having the optimal trajectory, the target tissue of the patient is divided along a line or plane parallel to the sagittal plane. FIG. 24 shows a map of the surfaces of target tissue on an S1 vertebra 1 of a specific patient used in designing device 10" of FIG. 17, on which the dividing line 80 has been indicated to pass through the center of the locus of bore 18 and to be parallel to the sagittal plane. From this, three points are selected on the surface of each side of the dividing line/plane 80, for a total of six point locations.

The points of contact ($M_1$, $M_2$, $M_3$, $M_4$, $M_5$, $M_6$) are selected to meet the following conditions: (1) each three of these points are located on one side ($S_1$ or $S_2$) of the plane 80 that divides the surface of contact into two surfaces through the planned sacral screw entry point (i.e., bore 18); (2) by defining $\theta_{ij}$ as the angle formed by any two normal vectors to the surface 24 of the device 10" at two different points $M_i$ and $M_j$, both on the same side $S_1$ or $S_2$, then cos $\theta_{ij} \leq \frac{1}{4}$ where $i \neq j$ and $i,j=1, 2 \ldots 6$; and (3) for each $M_i$ in $S_1$ and each $M_j$ in $S_2$, with $\vec{k}$ defined as the normal vector to the surface of contact at the point $M_i$, and $\vec{i}$, $\vec{j}$ are two normal vectors to the vector $\vec{k}$ with $\|i\|=\|j\|=\|k\|=1$ (with 1 unit=1 mm); and T is a transformation defined by a matrix M. Where M represents any combination of translations or rotations, and S is the surface of contact of the device along which it contacts the target tissues of the patient matching anatomy; $M_i'=T(M_i)$;

where ($x_i$, $y_i$, $z_i$) are the coordinates of $M_i'$ in the axis system $\vec{i}$, $\vec{j}$, $\vec{k}$;
if $-3<x_i<3$, $-3<y_i<3$ and $-3<z_i<3$;
and if $M_i' \in S$;
then $M_j' \notin S$ The same applies for each $M_j$ in $S_2$.
$M_j'=T(M_j)$ ($x_j$, $y_j$, $z_j$) are the coordinates of $M_j'$ in the axis system $\vec{i}$, $\vec{j}$, $\vec{k}$
if $-3<x_j<3$, $-3<y_j<3$ and $-3<z_j<3$
and if $M_j' \in S$
then $M_i' \notin S$.

Once these locations have been selected, then the device 10" is to have features that make contact at at least these predefined six contact points. Thus, anchors 22, indicators 26 and/or jaws 12J", 14J" may be configured to make contact with various of the preselected contact points. Therefore normal vectors defined coaxially with the anchors 22 or indicators 26 and vectors normal to jaw contact surfaces will meet the conditions (1) and (2) above. Meeting these constraints will ensure that at least the minimum amount of curvature of the target tissue surfaces to be contacted will have been met to define a unique proper position of the device 10" that is still relatively easy to orient the device 10" to.

Figure 25:
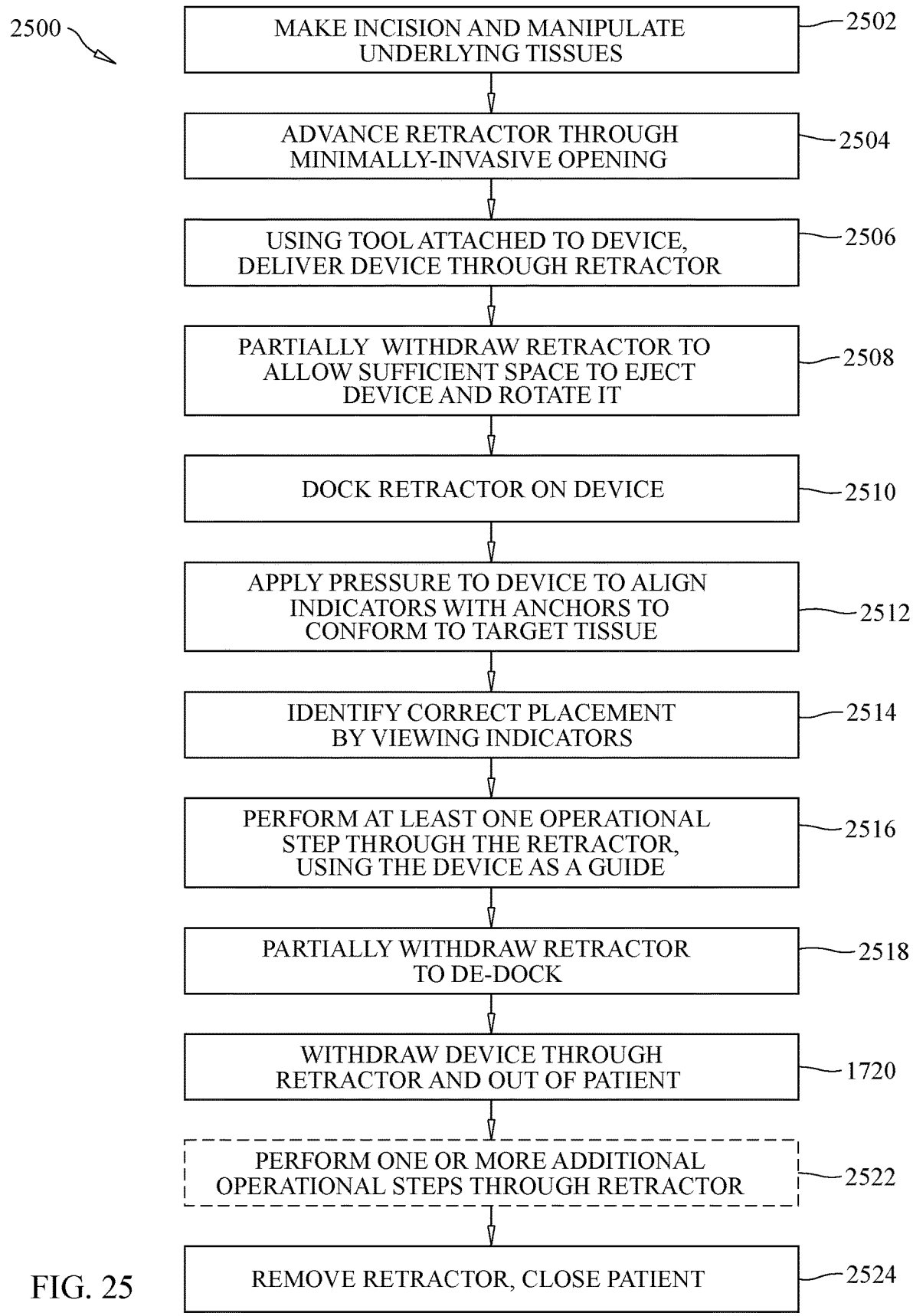
FIG. 25 is a flow chart illustrating events that may be carried out in performing a minimally-invasive surgical procedure according to an embodiment of the present invention.

FIG. 25 is a flow chart 2500 illustrating events that may be carried out in performing a minimally-invasive surgical procedure according to an embodiment of the present invention. At event 2502 an incision is made through the skin of a patient overlying the target tissue to be operated on and the tissues intermediate of the skin and the target tissue are manipulated to provide a minimally invasive opening to the target tissue. Optionally, a K-wire or other guide can be first inserted through the opening made by the incision and then dilators of increasing diameter can be subsequently used to increase the size of the pathway leading to the surgical target location (target tissue).

At event 2504, a slotted retractor/access port 70 is installed through the incision with or without use of the optional K-wire or other guide, and advanced through the minimally-invasive opening until a distal end of the slotted retractor/access port 70 contacts or is in close proximity to (3 mm or less) the target tissue for a posterior procedure. The retractor/port is maintained stationary relative to a stationary object outside of the patient, either by hand or by fixing relative to an external stationary object.

A device 10, 10', 10" may be connected to tool 50 or may have already been previously connected to tool 50 in preparation for delivering the device through the retractor/port 70 to the target tissue. At event 2506 the tool 50 is used to insert the device 10, 10', 10" into the retractor 70 and is delivered through the tubular structure of the retractor 70 into contact with the target tissue at event 2506. As noted, the device 10, 10', 10" can be an integral device that can be inserted in its entirety through the retractor in a single step. The tool 50 can be configured to rotate the device 10, 10', 10'', so that it can be oriented with a relatively small cross-section as it is delivered through the retractor 70 and then rotated to place the relatively larger cross-section of a contact surface in apposition with the target tissue once the device 10, 10', 10'' has been delivered out of the retractor 70. The retractor 70 may be slotted lengthwise with a slot 72 having a width that is sufficient to allow a shaft of the tool 50 to be freely slid along the length of the slot 72.

As the device 10, 10', 10'' is delivered to the distal end portion of the retractor 70, the retractor 70 is partially withdrawn at event 2508, e.g., by a distance in the range typically from 10 to 30 mm, to provide a gap between the distal end of the retractor 70 and the target tissue that is sufficient to allow the device 10, 10', 10'' to be delivered distally of the distal end of the retractor 70 and rotated to place the contact surface 24 in an orientation facing the target tissue. This allows the device 10, 10', 10'' to be delivered distally of the distal end of the retractor 70. While the device 10, 10', 10'' is being so delivered, the surgeon may at the same time (or after delivery distal of the distal end of the retractor) rotate the device 10, 10', 10'' so that the predefined contact surface is oriented to face the target tissue.

The device 10, 10', 10'' may be placed into contact with the target tissue in the orientation and position that it has been specifically contoured for using 3D customized manufacturing techniques referred to herein. The retractor 70 at event 2510 can next docked on the device 10, 10', 10'' by inserting portions of the distal end of the retractor 70 into the retractor mounts 30 described previously.

Pressure can be applied to the device 10, 10', 10'' before, during or after docking the retractor on the device 10, 10', 10'' at event 2512 to move it into the correct orientation in apposition with the target tissue, by aligning the sliding indicators with the anchors in conformity with the surface contour of the target tissue that the device 10, 10', 10'' is applied against. The correct orientation once achieved can be visibly verified when the surgeon sees each of the visual indicators 26P at event 2514.

Once the device 10, 10', 10'' has been correctly positioned in contact with the target tissue, at least one operational step can be performed on the target tissue through the retractor 70, while being guided by the device 10, 10', 10''. Operational steps may include drilling, screwing, rasping, cutting, cauterizing or many other known surgical procedural steps. In the embodiments described previously, guide 10, 10', 10'' is used as a drill guide. A K-wire or other guide can be used after the device 10, 10', 10'' has been placed and after the drilling is completed. For example, a K-wire can be used to guide delivery of a sacral screw or pedicle screw to the drilled hole.

Also, all or part of the insertion tool 50 may be used to guide one or more of the operational steps performed on the target tissue.

After completion of the one or more operational steps guided by the device 10, 10', 10'', the retractor 70 can be again slightly retracted at event 2518 to again provide a space between distal end 70D and the target tissue that is sufficient to allow the device 10, 10', 10'' to again be rotated by articulation of tool 50. The device 10, 10', 10'' can then be withdrawn out of the retractor/port 70 at event 2520.

After removal of the device 10, 10', 10'' from the port 70, one or more further operational steps may be performed through the retractor 70 at event 2522. For example, when the device is a guide that is used to guide the drilling of a hole into bone along an optimal axis for installation of a sacral screw, a sacral screw can be installed through the retractor/port 70 at event 2522 and torqued into the pathway so that it is anchored to the S1 vertebra along the optimal axis of implantation.

Upon completion of any additional operational steps at event 2522, the retractor/access port 70 can be disconnected from its anchoring to a stationary object and then the access port 70 is removed and the patient is closed according to standard procedures at event 2524.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A patient-specific, MIS navigation guide device comprising:
    a main body having a proximal surface and a distal surface, wherein said distal surface is configured to face target tissue upon placement of said MIS navigation guide device;
    anchors extending distally of said distal surface, wherein distal ends of said anchors lie on a three dimensional surface that matches contours of the target tissue in locations where the anchors are designed to contact; and
    a position indicator on said device;
    wherein said position indicator is interpretable by a surgeon to know when said anchors have not yet been contacted to the target tissue in a predetermined orientation and to know when the anchors have been contacted to the target tissue in the predetermined orientation.

2. The patient-specific, MIS navigation guide device of claim 1, further comprising a retractor mount configured to dock a retractor over said proximal surface of said device.

3. The patient-specific, MIS navigation guide device of claim 1, wherein said guide device is configured to guide the performance of a surgical operational step on the target tissue along an optimal predefined pathway.

4. The patient-specific, MIS navigation guide device of claim 1, wherein said position indicator comprises at least two position indicators with one of each at least two position indicators being located on an opposite side of said main body, relative to a location of another of said at least two position indicators.

5. The patient-specific, MIS navigation guide device of claim 1, further comprising:
    a first pair of generally opposing jaw surfaces formed on a first portion of said main body; and
    a second pair of generally opposing jaw surfaces formed on a second portion of said main body, wherein said second portion is on an opposite side of said main body to a side of said main body on which said first portion is located.

6. The patient-specific, MIS navigation guide device of claim 5, wherein said first pair of generally opposing jaw surfaces are configured to contact a specific spinous process of a specific vertebra of a specific patient and said second pair of generally opposing jaw surfaces are configured to contact a specific transverse process of the specific vertebra of the specific patient.

7. The patient-specific, MIS navigation guide device of claim 6, wherein the specific vertebra is the S1 vertebra.

8. The patient-specific MIS navigation guide device of claim 5, wherein said first pair of generally opposing jaw surfaces are configured to contact a specific process of a specific vertebra in the cervical spine of a specific patient and said second pair of generally opposing jaw surfaces are configured to contact another specific process of the specific vertebra in the cervical spine of the specific patient.

9. The patient-specific MIS navigation guide device of claim 5, wherein said first pair of generally opposing jaw surfaces are configured to contact a specific process of a specific vertebra in the thoracolumbar spine of a specific patient and said second pair of generally opposing jaw surfaces are configured to contact another specific process of the specific vertebra in the thoracolumbar spine of the specific patient.

10. The patient-specific, MIS navigation guide device of claim 1, further comprising a bore through said main body located to match a point of entry of a screw to be implanted in the target tissue; and
   a trajectory guide aligned with said bore and configured to guide a drill along an optimal axis of implantation of the screw in the target tissue.

11. The patient-specific, MIS navigation guide device of claim 10, configured to contact the target tissue on at least six predefined locations ($M_1$, $M_2$, $M_3$, $M_4$, $M_5$, $M_6$) conforming to the following conditions:
   at least three of the at least six predefined locations are located on one side of said device, relative to said bore;
   at least three others of the at least six predefined locations are located on an opposite side of said device, relative to said bore;
   said one side and said opposite side are defined relative to a line that passes through said bore and is aligned with the sagittal plane of the patient, when said device is mounted as desired relative to the target tissue; and
   for locations $M_i$ and $M_j$ both located on the same one of said sides,
   $\cos \theta_{ij} \leq 1/4$
   where $i \neq j$ and $i,j = 1, 2 \ldots 6$;
   $\theta_{ij}$ is the angle formed by any two normal vectors to the surface of said device, respectively, at locations $M_i$ and $M_j$;
   for each $M_i$ on said one side each $M_j$ on said opposite side, with $\vec{k}$ defined as a normal vector to a surface of contact on the target tissue at the point $M_i$ where said device contacts the target tissue, and $\vec{i}$, $\vec{j}$ are two normal vectors to the vector $\vec{k}$ with $\|i\|=\|j\|=\|k\|=1$ (with 1 unit=1 mm);
   wherein T is a transformation defined by a matrix M, where M represents any combination of translations or rotations, and S is a surface of contact of said device along which it contacts matching anatomy of the target tissue; $M_i' = T(M_i)$;
   where ($x_i$, $y_i$, $z_i$) are the coordinates of $M_i'$ in the axis system $\vec{i}$, $\vec{j}$, $\vec{k}$;
   if $-3 < x_i < 3$, $-3 < y_i < 3$ and $-3 < z_i < 3$;
   and if $M_i' \in S$;
   then $M_j' \notin S$; and
   $M_j' = T(M_j)$ ($x_j$, $y_j$, $z_j$) are the coordinates of $M_j'$ in the axis system $\vec{i}$, $\vec{j}$, $\vec{k}$
   if $-3 < x_j < 3$, $-3 < y_j < 3$ and $-3 < z_j < 3$;
   and if $M_j' \in S$;
   then $M_i' \notin S$.

12. The patient-specific, MIS navigation guide device of claim 7 in combination with a tubular MIS retractor, wherein said guide device is configured to be delivered through said tubular MIS retractor to the target tissue by an MIS surgical procedure.

13. The patient-specific, MIS navigation guide device of claim 7 in combination with an MIS delivery tool, wherein said delivery tool is configured to releasably attach to said guide device and is articulatable to rotate an orientation of said guide device.

14. The device and tool of claim 13 configured for use in MIS percutaneous spine surgeries.

15. A minimally-invasive surgical procedure comprising:
   inserting an MIS retractor through an incision and into a pathway formed in a patient over target tissue until a distal end of the retractor contacts or approximates the target tissue;
   delivering an MIS, patient-specific device through the retractor using a tool releasably attached to the device;
   partially withdrawing the MIS retractor to define a space between the distal end of the retractor and the target tissue sufficient to deliver the device into;
   rotating the device when the device is distal of the distal end of the retractor and contacting the device to the target tissue, wherein the target tissue is of a specific vertebra of a specific patient;
   docking the retractor into a mating feature of the device; and
   performing at least one operational step on the specific vertebra through the retractor, guided by the MIS, patient-specific device.

16. The procedure of claim 15, wherein the specific vertebra is the S1 vertebra of the specific patient.

17. The procedure of claim 15, wherein the specific vertebra is located in the cervical spine of the specific patient.

18. The procedure of claim 15, wherein the specific vertebra is located in the thoracolumbar spine of the specific patient.

19. The procedure of claim 15, further comprising:
   again partially withdrawing the MIS retractor to define a space between the distal end of the retractor and the target tissue; and
   withdrawing the device through the retractor and out of the patient.

20. The procedure of claim 15, further comprising:
   performing one or more further operational steps on the specific patient through the retractor.

* * * * *